United States Patent
Babich et al.

(10) Patent No.: US 9,687,572 B2
(45) Date of Patent: Jun. 27, 2017

(54) PSMA-TARGETED DENDRIMERS

(75) Inventors: John W. Babich, Tarrytown, NY (US); John L. Joyal, Melrose, MA (US); Craig Zimmerman, Topsfield, MA (US)

(73) Assignee: MOLECULAR INSIGHT PHARMACEUTICALS, INC., Cambridge, MA (US)

( * ) Notice: Subject to any disclaimer, the term of this patent is extended or adjusted under 35 U.S.C. 154(b) by 1057 days.

(21) Appl. No.: 13/991,812

(22) PCT Filed: Dec. 6, 2011

(86) PCT No.: PCT/US2011/063361
§ 371 (c)(1),
(2), (4) Date: Aug. 20, 2013

(87) PCT Pub. No.: WO2012/078534
PCT Pub. Date: Jun. 14, 2012

(65) Prior Publication Data
US 2013/0336888 A1    Dec. 19, 2013

Related U.S. Application Data

(60) Provisional application No. 61/420,265, filed on Dec. 6, 2010.

(51) Int. Cl.
    A61K 51/04    (2006.01)
    A61K 51/06    (2006.01)

(52) U.S. Cl.
    CPC ........ A61K 51/0497 (2013.01); A61K 51/065 (2013.01)

(58) Field of Classification Search
    CPC .................. A61K 51/0497; A61K 51/065
    See application file for complete search history.

(56) References Cited

FOREIGN PATENT DOCUMENTS

WO    WO-2010/065902 A2    6/2010

OTHER PUBLICATIONS

Xu et al., Exp Biol Med, 2007, 232, p. 1081-1089.*
Kularatne et al., Molecular Pharmaceutics, 2009, 6(3), p. 780-789.*
C. Wangler et al: "Antibody-Dendrimer Conjugates: The Number, Not the Size of the Dendrimers, Determines the Immunoreactivity", Bioconjugate Chemistry, vol. 19, No. 4, Apr. 1, 2008, pp. 813-830, XP55020206.
Heng Xu et al: "Preparation and Preliminary Evaluation of a Biotin-Targeted, Lectin-Targeted Dendrimer-Based Probe for Dual-Modality Magnetic Resonance and Fluorescence Imaging", Bioconjugate Chemistry, Vo. 18, No. 5, Sep. 1, 2007, pp. 1474-1482, XP55020181.
Maresca K P et al: "A series of halogenated Heterodimeric inhibitors of prostate specific membrane antigen (PSMA) as radiolabeled probes for targeting prostate cancer", Journal of Medicinal Chemistry, American Chemical Society, US, vol. 52, Jan. 22, 2009, pp. 347-357, XP002614472.
Patri A K et al: "Synthesis and In Vitro Testing of J591 Antibody-Dendrimer Conjugates for Targeted Prostate Cancer Therapy", Bioconjugate Chemistry, ACS, Washington, DC, US, vol. 15, No. 6, Jan. 1, 2004, pp. 1174-1181, XP008041448.
PCT/US2011/063361—International Search Report—mailed Mar. 5, 2012.
S. M. Hillier et al: "Preclinical Evaluation of Novel Glutamate-Urea-Lysine Analogues That Target Prostate-Specific Membrane Antigen as Molecular Imaging Pharmaceuticals for Prostate Cancer", Cancer Research, Vo. 69, No. 17, Sep. 1, 2009, pp. 6932-6940, XP5502196.
Sachin S. Chandran et al: "Characterization of a targeted nanoparticle functionalized with a urea-based inhibitor of prostate-specific membrane antigen (PSMA)", Cancer Biology & Therapy, vol. 7, No. 6, Jun. 1, 2008, pp. 974-982, XP55020248.
Office Action issued in co-pending Japanese application No. 2013-542250 dated Jul. 28, 2015 with English translation.

* cited by examiner

*Primary Examiner* — Michael G Hartley
*Assistant Examiner* — Leah Schlientz
(74) *Attorney, Agent, or Firm* — Gilberto M. Villacorta; Jeffrey R. Lomprey

(57) ABSTRACT

A dendrimer conjugate according to Formula (I), or its pharmaceutically acceptable salt, or solvate thereof: and complexes of Formula I conjugates with metals radionuclides of elements such as rhenium, technetium, yttrium, lutetium and others to provide a complex for imaging tissues or for the radiotherapeutic treatment of cancer tissue. Such complexes are specific to PSMA protein and can therefore be used in imaging or treating cancer of the prostate and other tissue where the protein is expressed.

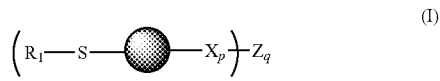

(I)

25 Claims, 1 Drawing Sheet

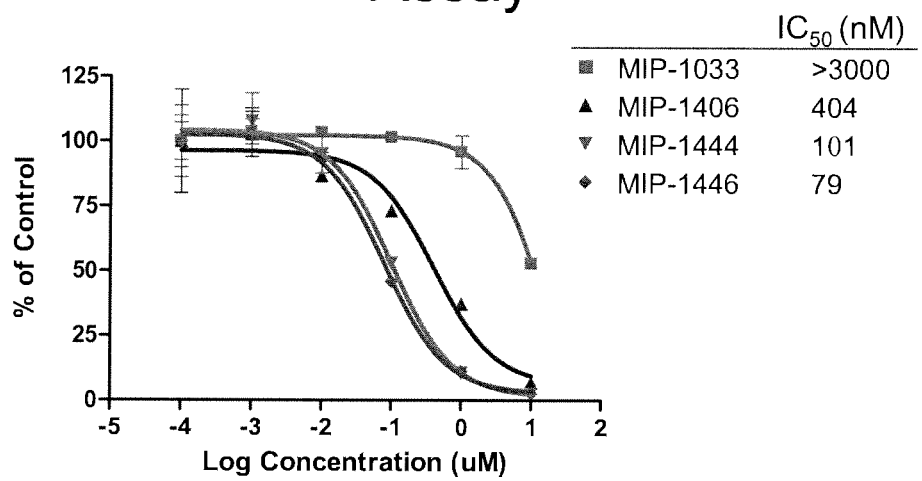

PSMA-TARGETED DENDRIMERS

CROSS-REFERENCE TO RELATED PATENT APPLICATIONS

This application claims priority from U.S. Provisional Application 61/420,265, filed Dec. 6, 2010, incorporated herein by reference in its entirety.

BACKGROUND OF THE INVENTION

The present invention relates generally to the field of radiopharmaceuticals and their use in nuclear medicine as tracers, imaging agents and for the treatment of various disease states. It is well known that tumors may express unique proteins associated with their malignant phenotype or may over-express normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins provide an attractive route for imaging and treating tumors under non-invasive conditions. In particular, the present inventors have found that radiolabeled ligands to the PSMA protein, often over expressed on prostate cancer cells and the vasculature of other types of solid tumors provide an attractive route for non-invasive imaging and selective targeting of cancer cells.

At least 1 million men suffer from prostate cancer and it's estimated that the disease will strike one in six U.S. men between the ages of 60 and 80. There are more than 300,000 new cases of prostate cancer diagnosed each year. Prostate cancer will affect one in six men in the United States, and the mortality from the disease is second only to lung cancer. An estimated $2 billion is currently spent worldwide on surgical, radiation, drug therapy and minimally invasive treatments, $1 billion of the spending in the U.S. There is presently no effective therapy for relapsing, metastatic, androgen-independent prostate cancer. New agents that will enable rapid visualization of prostate cancer and specific targeting to allow radiotherapy present are needed.

PSMA, also known as folate hydrolase I or glutamate carboxypeptidase II is a transmembrane, 750 amino acid type II glycoprotein which is primarily expressed in normal human prostate epithelium, and is upregulated in prostate cancer, including metastatic disease (4-6). It has been reported that over expression of PSMA in primary prostate cancer correlates with other adverse traditional prognostic factors and independently predicts disease outcome (7). Since PSMA is expressed by virtually all prostate cancers and its expression is further increased in poorly differentiated, metastatic and hormone-refractory carcinomas (8-10), it is a very attractive target for developing radiopharmaceuticals for the diagnosis, staging and treatment of the disease.

PSMA is highly homologous to N-acetylated α-linked acidic dipeptidase (NAALADase), a neuropeptidase which produces the neurotransmitter glutamate and N-acetylaspartate through the hydrolysis of N-acetylaspartylglutamate. Analysis of the crystal structure of PSMA has aided in the understanding of the critical interactions of potent inhibitors within the active site of the enzyme and has led to the design and synthesis of several classes of NAALADase inhibitors that are substrate or transition state analogs.

Radiolabeled anti-PSMA monoclonal antibodies, like Prostascint which is approved by the FDA for diagnostic imaging, and J591 which is in clinical trials for targeted radiotherapy of metastatic prostate cancer (11, 12), have validated PSMA as molecular target for prostate cancer. However, while monoclonal antibodies offer potential for tumor targeting, long circulating half-life and poor tumor penetrability, particularly for bone metastases, limit their effectiveness as diagnostic and therapeutic radiopharmaceuticals (13). For these reasons, there have been only limited clinical successes to date with radiolabeled antibodies, mostly in the treatment of blood-borne cancers such as non-Hodgkin's lymphoma (14).

Small molecules offer significant advantages over antibodies for targeting solid tumors (15). They can be designed with affinities similar to that of monoclonal antibodies. Small molecules exhibit enhanced diffusibility to the extravascular space, and faster blood clearance than antibodies, thus resulting in lower background signal. However, studies carried out by the present inventors as well as others have shown that radiolabeled small molecule PSMA inhibitors exhibit high uptake in the kidneys which has a high expression of the PSMA protein. Accordingly, the kidneys may function to limit a therapeutically effective dose of the radiopharmaceutical from reaching the target tissue.

The present invention overcomes the stated drawback of small molecule PSMA inhibitors by providing the synthesis of a series of dendrimer conjugates of the inventive PSMA inhibitors. Also described are the synthesis of tetramers of the inventive PSMA compounds as well as pharmaceutical compositions of the inventive dendrimers and methods for using the inventive compositions to treat, diagnose and image prostate cancer tissue.

SUMMARY OF THE INVENTION

The present invention provides a PSMA-targeting/recognition moiety that is conjugated to a dendrimer according to Formula I:

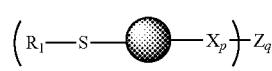

In Formula I, ● represents the dendrimer core of a generation, n, selected from the group consisting of generation 1, 2, 3, 4, 5, 6, 7, 8, 9 and 10. Each generation of the dendrimer is associated with a predetermined number of surface groups, p. Substituent X is selected from the group consisting of —COOR', —NR'R", in its "free" or unconjugated form and —NHC(O)—$(CH_2)_a$—C(O)—, —NHC(O)—$(C_2-C_6)$alkenyl-C(O), —NHC(O)—$CH_2$—O—$NH_2$, —NHC(O)—$(CH_2)_a$-maleimide, and —NR'—$(CH_2)_a$—NR" in its conjugated form.

S is sulfur. Substituent $R_1$ is a metal chelator and p is an integer selected from 4, 8, 16, 32, 64, 128, 256, 512, 1024, 2048 and 4096. Substituent Z is a prostate specific membrane antigen targeting moiety according to Formula A:

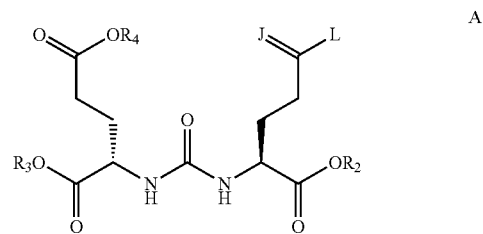

For Formula A compounds, —C=J is —CH$_2$ group or —C=O group and L is selected from the group consisting of —COOR''', —(CH$_2$)—NH—C(O)—CH(O)—, —(CH$_2$)—NH—C(O)—(CH$_2$—CH$_2$—O)$_y$—NR'—, —(CH$_2$)—NH—C(O)—(CH$_2$)$_z$—NR'—; and —(CH$_2$)—NH—C(O)—(CH$_2$)$_z$—SH—.

Each of R', R'', R''', R$_2$, R$_3$, and R$_4$ are independently selected from the group consisting of H, and straight or branched C$_1$-C$_6$ alkyl and q represents the proportion of available surface groups, X, conjugated to Z. Subscripts a, y and z are each independently integers between 0 and 8 inclusive.

In another embodiment, an inventive dendrimer conjugate is provided wherein Y is —NHC(O)—(CH$_2$)$_a$C(O)— and Z is a Formula A compound in which —C=J is —CH$_2$ and L-(CH$_2$)—NH—C(O)—(CH$_2$)$_z$—NR'—.

In yet another embodiment, R$_1$ is a polyaminocarboxylic acid chelator such as the group DOTA whose structure is shown below:

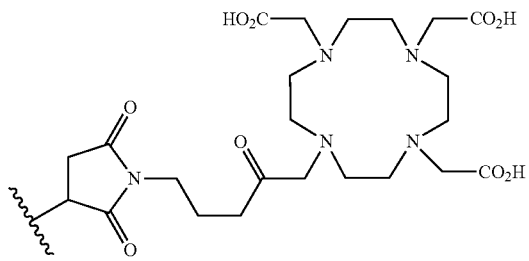

Pursuant to another embodiment, the invention provides a complex comprising (i) a metal ion; and (ii) a dendrimer conjugate according to according to Formula I:

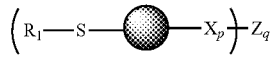

I

Groups R$_1$, X, and Z as well as subscripts p and q are as defined above. According to this aspect, the metal is selected from the group consisting of $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{68}$Ga, $^{111}$In and $^{188}$Re. While any suitable metal chelator can be used to complex the radionuclide, in one embodiment R$_1$ is DOTA.

The invention also provides a pharmaceutical formulation, comprising the inventive dendrimer-radionuclide complex along with a pharmaceutically acceptable salt or solvate thereof, and a pharmaceutically acceptable excipient.

Also provided is a method for treating prostate cancer in a patient, comprising administering to a patient a therapeutically effective amount of a pharmaceutical composition of the inventive complex, or a pharmaceutically acceptable salt or solvate thereof in which the radionuclide (M) is selected from the group consisting of $^{90}$Y, $^{86}$Y, $^{177}$Lu, $^{188}$Re, $^{186}$Re, $^{99m}$Tc, $^{111}$In, $^{68}$Ga, $^{64}$Cu, $^{67}$Cu, $^{212}$Pb, $^{203}$Pb, $^{212}$Bi, $^{89}$Zr.

The present invention further provides a method of imaging prostate cancer tissue in a patient, comprising administering to a patient a diagnostically effective amount of a pharmaceutical composition of the inventive complex, or a pharmaceutically acceptable salt or solvate thereof in which radionuclide (M) is selected from the group consisting of $^{68}$Ga, $^{111}$In and $^{186}$Re, and obtaining an image of said prostate tissue. Preferably, the tissue to be imaged is a PSMA expressing tissue, such as a PSMA-expressing prostate cancer tissue.

BRIEF DESCRIPTION OF THE DRAWINGS

FIG. 1 is a graph that illustrates competitive binding of several of the inventive compounds to PSMA in the presence of radiolabelled MIP 1072

DETAILED DESCRIPTION OF THE PREFERRED EMBODIMENTS

I. Definitions

For convenience, certain terms employed herein and within the appended claims are collected here.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The use of the terms "a" and "an" and "the" and similar referents in the context of describing the elements (especially in the context of the following claims) are to be construed to cover both the singular and the plural, unless otherwise indicated herein or clearly contradicted by context.

The term "attached" refers to a connection between chemical components of the macromolecule, such as the dendrimer and the PSMA inhibitor by way of covalent bonding, hydrogen bonding, adsorption, metallic bonding, Van der Waals forces, ionic bonding, or any combination thereof. In one embodiment attachment is through the formation of a covalent bond. The attachment between dendrimer and PSMA inhibitor may be direct, or indirect, that is, through an intervening moiety or moieties, such as a bridge, spacer, or linker moiety or moieties, which terms may be used interchangeably herein. Furthermore, a linker group or functional moiety or amine may be further modified by a modifier to facilitate the attachment.

The term "selected point of attachment" refers to an amine and/or carboxyl group or amine and/or carboxyl groups on the dendrimer polymer that are differentiated from other amine groups of the dendrimer polymer in being uniquely reactable at a defined stage in the synthesis of the dendrimer polymer, thereby allowing the attachment of a functional moiety or dendritic motif. This advantageously allows the surface position and distribution of a functional moiety to be known. The selected point of attachment may therefore be at the first nitrogen atom of the core moiety or on the surface of the dendrimer.

The term "binding" as used herein in the specification and claims refers to the ability of a given molecule to be captured (bound) and held by another, for example a ligand to interact with a target such that the interaction between the ligand and its target is relatively specific. Examples include the specific interaction between an antibody, or derivatives and fragments thereof and the antibody target (receptor); or the interaction between a small molecule, such as biotin, folate, or PSMA inhibitor, and their respective targets.

The term "lysine analog" refers to a molecule which has a single apex carboxyl group and can have two or three primary amine groups. In one instance, the lysine analog is a compound in which the side chain is extended at the epsilon amino group to include a —C(O)—CH(O)—, —C(O)—(CH$_2$—CH$_2$—O)$_y$—NR'—, —C(O)—(CH$_2$)$_z$—NR'—; and —C(O)—(CH$_2$)$_z$-group.

As used herein, the term "layer" or "generation" of a dendrimer refers to a plurality of building units having the same degree of connectivity to the core moiety, i.e. having the same number of building units linking the building unit in question to the amino nitrogen atoms of the core. For example, building units which are attached, either directly or via a linker group, to the nitrogen atoms of the core moiety are referred to the first layer or generation. Building units which have one building unit between them and the nitrogen atoms of the core moiety are referred to as the second layer or generation. A layer or generation of building units must contain at least two building units. Each layer of building units is homogenous with regard to the building unit used, however, different building units may be used to prepare different layers. Thus in certain embodiments of the invention, the macromolecule is composed of one or more layers of a single type of building unit. In other embodiments, the macromolecule comprises at least two layers of building units wherein at least two layers are composed of different building units.

The term "surface" as used herein, is used in reference to the outermost layer of building units of the dendrimer.

The terms "surface group" or "surface building unit" refers to groups present in the outermost layer of the dendrimer. The surface groups can be free amines, carboxyl groups, or the reaction product of these groups with an appropriate intervening moiety or moieties, such as a bridge, spacer, or linker moiety or moieties, which terms may be used interchangeably herein.

The term "surface amine" or "surface amino" or "surface amino nitrogen atom" refers to any of the outer-most nitrogens of the dendritic motif. These surface amines represent the points of attachment for additional building units, linkers or functional moieties.

The term "functional moiety" as used herein in the specification and claims refers to any group, as defined herein, that may be attached, either directly or indirectly, at a first amino nitrogen of the core or a surface amine with the purpose of serving the stated function. The nature and number of functional moieties may be determined by standard analytical techniques including proton/carbon NMR, ESI or MALDI mass spectrometry.

The terms "lipophilic group" and "lipophilic moiety" as used herein refer to a group, moiety or substituent that has a greater affinity for non-polar or non-aqueous environments versus polar or aqueous environments. For example, Merriam Webster's online dictionary defines "lipophilic" as "having an affinity for lipids (as fats)." Exemplary lipophilic moieties include aliphatic hydrocarbon radicals, e.g., alkyl radicals, aromatic hydrocarbon radicals, and long-chain acyl radicals; all of them have increasing lipophilicity as the number of constituent carbons increases. In general, addition of a lipophilic moiety to a particular compound will increase the compound's affinity for octanol in the standard octanol/water partition-coefficient-determination protocol; this protocol may be used to gauge a compound's relative hydrophobicity (lipophilicity) and hydrophilicity.

The term "ligand" refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The term "complex" refers to a compound formed by the union of one or more electron-rich and electron-poor molecules or atoms capable of independent existence with one or more electronically poor molecules or atoms, each of which is also capable of independent existence.

Fmoc is an abbreviation for the chemical group: fluorenylmethyloxycarbonyl.

The phrase "therapeutically-effective amount" as used herein means that amount of a compound, material, or composition comprising a compound which is effective for producing some desired therapeutic effect in at least a sub-population of cells in an animal at a reasonable benefit/risk ratio applicable to any medical treatment.

As used herein, the terms "treating" or "treatment" is intended to encompass also diagnosis, prophylaxis, therapy and cure. The patient receiving this treatment is any animal in need, including primates, in particular humans, and other mammals such as equines, cattle, swine and sheep; and poultry and pets in general.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "amino acid" refers to all compounds, whether natural or synthetic, which include both an amino functionality and an acid functionality, including amino acid analogs and derivatives.

The term "heteroatom" refers to an atom of any element other than carbon or hydrogen. Illustrative heteroatoms include boron, nitrogen, oxygen, phosphorus, sulfur and selenium.

In general, "substituted" refers to an alkyl or alkenyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Alkenyl groups may be substituted or unsubstituted. Representative substituted alkenyl groups may be mono-substituted or substituted more than once, such as, but not limited to, mono-, di- or tri-substituted with substituents such as those listed above.

The term "amine or amino" refers to an —NR$^c$R$^d$ group wherein R$^c$ and R$^d$ each independently refer to a hydrogen, (C$_1$-C$_8$)alkyl, aryl, heteroaryl, and heterocycloalkyl group. When R$^c$ and R$^d$ are attached to the same nitrogen atom, they can be combined with the nitrogen atom to form a 5-, 6- or 7-membered ring. For example, —NR$^c$R$^d$ is meant to include 1-pyrrolidinyl, pyridinyl or a 4-morpholinyl ring.

The term "amido" is art recognized as an amino-substituted carbonyl and includes a moiety that may be represented by the general formula, —C(O)NR$^c$R$^d$ group wherein R$^c$ and R$^d$ are as defined above. According to some embodiments, the amide does not include imides which may be unstable.

The terms "carboxyl" and "carboxylate" are include such moieties as may be represented by the general formulas:

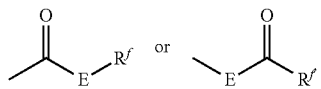

wherein E is a bond or represents O or S, and R$^f$ and R$^{f'}$ individually is H, alkyl, alkenyl, or a pharmaceutically acceptable salt. Where E is O, and R$^f$ is as defined above, the moiety is referred to herein as a carboxyl group, and particularly when R$^f$ is a hydrogen, the formula represents a "carboxylic acid". In general, where the expressly shown oxygen is replaced by sulfur, the formula represents a "thiocarbonyl" group.

The terms "alkoxyl" or "alkoxy" refer to an alkyl group, as defined above, having an oxygen radical attached thereto. Representative alkoxyl groups include methoxy, ethoxy, propoxy, butyoxy, tert-butoxy and the like. An "ether" is two hydrocarbons covalently linked by an oxygen. "Ether" also encompasses polyethers where more than one ether group, or linkage, may be present in a given group. "Ether" also encompasses cyclic ethers, and crown ethers, where the ether linkage is within a cyclic group.

Certain compounds contained in the compositions may exist in particular geometric or stereoisomeric forms. In addition, compounds may also be optically active. The compounds may also include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. If, for instance, a particular enantiomer of compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 3rd* ed.; Wiley: New York, 1999).

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

II. Inventive Compounds and Dendrimer Conjugates

The present invention is directed to novel PSMA targeting moities, and to the synthesis of a chelator-dendrimer conjugates of the PSMA targeting moieties. In particular the chelator group is one which effectively chelates a variety of metal ions that are used in radioimaging applications and as radiopharmaceuticals for treatment of disease states.

Also encompassed within the scope of the present invention are pharmaceutically acceptable compositions of the inventive radiolabel containing chelator-dendrimer-PSMA targeting conjugates as well as methods for using the inventive composition to image and/or diagnose prostate cancer tissue, as well as to provide radiotherapeutic treatment for prostate cancer.

In particular, the inventive PSMA targeting moieties are glutamate urea homodimers (GUG), or glutamate urea heterodimers, such as a glutamate-urea-lysine dimer (GUL). In one aspect, therefore, the present invention describes the synthesis of the GUL and GUG PSMA targeting moieties as well as methodologies for the synthesis of di-, tri-, or tetramers of these moieties using an EDTA core.

Without being bound to any particular theory, the present inventors hypothesized that the distance of the GUL and GUG moieties from the dendrimer's surface groups could be important for binding to PSMA protein. To explore the optimal distance required for tight binding of the GUL/GUG-dendrimer conjugate to PSMA, the present inventors first synthesized and tested a series of GUL/GUG-EDTA conjugates in which the GUL or GUG moieties are bound directly to EDTA or via linkers of varying lengths. Thus, in one embodiment, GUL was directly conjugated to EDTA. In an alternate embodiment, the GUL or GUG moities are conjugated to EDTA via linkers. When GUL is the PSMA targeting moiety, linkers such as amino propionic acid or aminohexanoic acid are allowed to react with the $\epsilon$-amino group of lysine prior to conjugation with EDTA. When GUG is the PSMA targeting moiety, however, the carboxylate side chain of glutamic acid can be extended by reacting the $\gamma$-carboxyl group with 1,3-diaminopropoane or a diaminohexane linker prior to tetramerization using EDTA.

The binding affinities of the EDTA-tetramers of GUL, GUG, and those obtained using linkers of varying lengths were tested using LNCaP cell based assay as further explained below.

In yet another embodiment of the present invention, the GUG and GUL analogs are further conjugated to a dendrimer. Exemplary of suitable dendrimers are the starbust dendrimers, such as a cystamine core poly(amidoamine) PAMAM dendrimer. The PAMAM dendrimers are polymers that have a uniform macromolecular architecture known as a dense star polymer. The uniformity of the molecular architecture allows dendrimers to have a high degree of molecular uniformity, narrow molecular weight distribution, specific size and shape characteristics, and a highly-functionalized terminal surface. Each dendrimer is manufactured by a series of repetitive steps starting with a central initiator core. Each subsequent growth step represents a new "generation" of polymer with a larger molecular diameter, twice the number of reactive surface sites, and approximately double the molecular weight of the preceding generation.

The Table 1 below shows the calculated physicochemical properties of amine surface functional PAMAM dendrimers for each generation.

| Generation | Molecular Weight | Measured Diameter (Å) | Surface Groups |
|---|---|---|---|
| 0 | 517 | 15 | 4 |
| 1 | 1,430 | 22 | 8 |
| 2 | 3,256 | 29 | 16 |
| 3 | 6,909 | 36 | 32 |

-continued

| Generation | Molecular Weight | Measured Diameter (Å) | Surface Groups |
|---|---|---|---|
| 4 | 14,215 | 45 | 64 |
| 5 | 28,826 | 54 | 128 |
| 6 | 58,048 | 67 | 256 |
| 7 | 116,493 | 81 | 512 |
| 8 | 233,383 | 97 | 1024 |
| 9 | 467,162 | 114 | 2048 |
| 10 | 934,720 | 135 | 4096 |

In particular, a series of DOTA-conjugated PAMAM dendrimers functionalized with glutamate-urea-lysine (GUL) or glutamate-urea-glutamate (GUG) with molecular weights between 5,000-100,000 Da to identify a molecule which exhibits high affinity for PSMA, rapid clearance from the blood and non-target tissues, and reduced kidney uptake compared to molecular imaging radiopharmaceuticals currently in the clinic, for targeted radiotherapy of prostate cancer.

The present inventors realize that several features are desired in the design and development of synthetic dendrimers incorporating the GUL or GUG PSMA binding motifs. For example, conjugation of the PSMA targeting moiety to a dendrimer should allow the rapid synthesis of conjugates having a defined size, number of surface charge groups, molecular weight, and the ability to readily alter the dendrimer-conjugate size based on the generation number of dendrimer used. Accordingly, inventive dendrimer conjugates can be rapidly evaluated to determine the correlation between molecular weight of the conjugate on tissue distribution, pharmacokinetics and clearance for the dendrimer-PSMA targeting conjugates.

Another criteria that will be evaluated for the inventive dendrimer conjugates is the influence of increasing number of PSMA targeting motifs on the affinity/avidity of binding.

The ability to tether a single metal chelator to the inventive dendrimer-PSMA targeting conjugate is important for many radiopharmaceutical applications. The present invention provides a methodology for synthesizing a chelator-dendrimer-PSMA targeting conjugates for radiolabeling studies using a any one of the metal radioisotopes mentioned below. Although any dendrimer can be used to synthesize chelator-dendrimer-PSMA targeting complexes in accordance with the present invention, the commercially available PAMAM dendrimers with a cystamine core and surface succinamic acid residues have been used to synthesize Formula I conjugates. These dendrimers are ideal as they provide single attachment point for the radioisotope chelator through the reaction of a free sulfhydryl group produced by reduction of the core disulfide bond. To lower in vivo toxicity, normally associated with free amine surface groups of the PAMAM dendrimer, the present inventors first modify the surface amino groups by reaction with excess succinic acid or an activated derivate such as succinic anhydride followed by coupling of the resultant succinamic acid residues with GUL.

Accordingly, the present invention describes the synthesis of a PSMA-dendrimer conjugate according to Formula I, or its pharmaceutically acceptable salts and solvates.

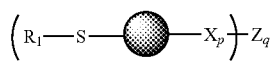

I

For Formula I conjugates ● represents the dendrimer core of a generation, n. The dendrimer selected for conjugation to the PSMA inhibitor has a fixed number of surface groups depending on the generation of the dendrimer used. The present invention describes dendrimer conjugates using any generation of the dendrimer, such as dendrimers belonging to generations 1, 2, 3, 4, 5, 6, 7, 8, 9, or 10.

For Formula I compounds, X is selected from the group consisting of —COOR', —NR'R", in its "free" or unconjugated form and —NHC(O)—(CH$_2$)$_a$—C(O)—, —NHC(O)—(C$_2$-C$_6$)alkenyl-C(O), —NHC(O)—CH$_2$—O—NH$_2$, —NHC(O)—(CH$_2$)$_a$-maleimide, and —NR'—(CH$_2$)$_a$—NR" in its conjugated form. S is sulfur or sulfhydryl group (—SH group). The metal chelator R$_1$, is attached to the dendrimer through the sulfhydryl group.

Integer p represents the number of surface groups present in a given generation of the dendrimer. Typically, the number of surface groups for Formula I dendrimers is 4, 8, 16, 32, 64, 128, 256, 512, 1024, 2048 and 4096 depending on the generation of dendrimer used.

For the inventive conjugates, the PSMA targeting moiety (Z), is a compound according to Formula A:

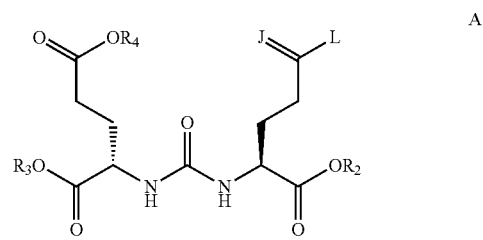

A

For Formula A compounds —C=J is either a —CH$_2$ group or —C=O group. L is selected from the group consisting of —COOR''', —(CH$_2$)—NH—C(O)—CH(O)—, —(CH$_2$)—NH—C(O)—(CH$_2$—CH$_2$—O)$_y$—NR'—, —(CH$_2$)—NH—C(O)—(CH$_2$)$_z$—NR'—; and —(CH$_2$)—NH—C(O)—(CH$_2$)$_z$—SH—. Substituents R', R", R''', R$_2$, R$_3$, and R$_4$ are each independently selected from the group consisting of H, and straight or branched C$_1$-C$_6$ alkyl.

Integer q, represents the proportion of available surface groups, X, conjugated to Z. According to one embodiment, therefore, proportion of available surface groups, X, conjugated to Z is in the range from about 10% to about 100%, preferably about 10%, 20%, 30%, 40%, 50%, 55%, 60%, 65% 70%, 75%, 80%, 85%, 90%, 92%, 94%, 96%, 98% or 99%. In one embodiment the proportion of available surface groups, X, conjugated to Z is in the range from about 50%, 52%, 54%, 56%, 58%, 60%, 62%, 64%, 66%, 68%, 70%, 72%, 74%, 76%, 78%, 80% 82%, 84%, 86%, or 88%. Furthermore, subscripts a, y and z are each independently integers between 0 and 8 inclusive.

For Formula I conjugates, the metal chelator can be a bidentate compound, a tridentate compound or a tetradentate compound having two or more unshared electron pairs which available for donation to a metal ion. The metal ion is usually coordinated by two or more electron pairs to the chelating agent.

Exemplary of metal chelator groups for Formula I conjugates are those selected from the group consisting of DOTA, DTPA, EDTA, cyclohexyl DTPA, hydroxamic acid chelators, deferrioxamine, hynic, thiosemicarbazone, TETA, NOTA, Mag3, and N2S2. Exemplary structures are shown in Table 2:

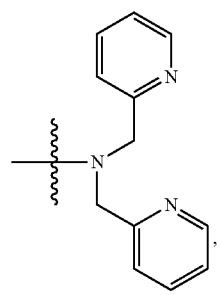 [SMILES: *N(Cc1ccccn1)Cc1ccccn1]
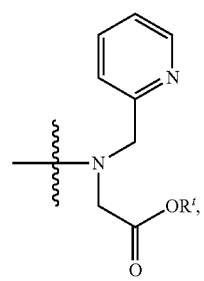
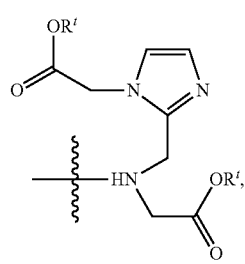
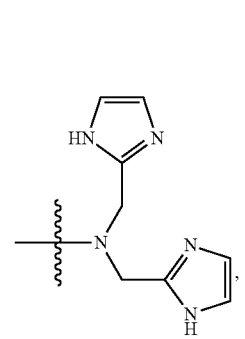 [SMILES: *N(Cc1ncc[nH]1)Cc1ncc[nH]1]
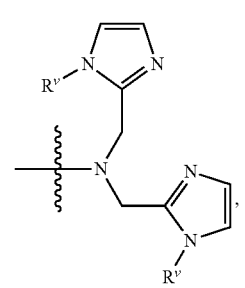
-continued
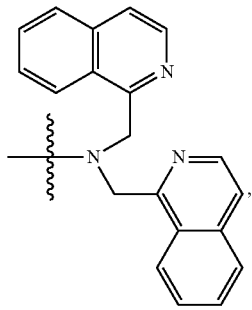 [SMILES: *N(Cc1nccc2ccccc12)Cc1nccc2ccccc12]
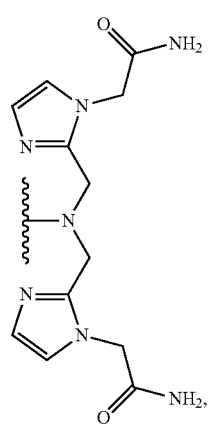 [SMILES: *N(Cc1nccn1CC(N)=O)Cc1nccn1CC(N)=O]
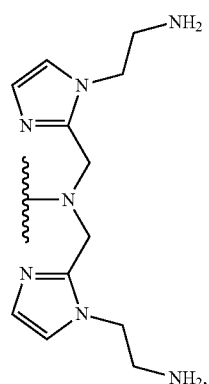
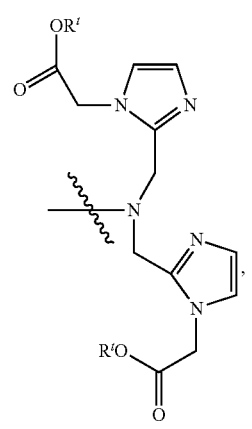

15
-continued

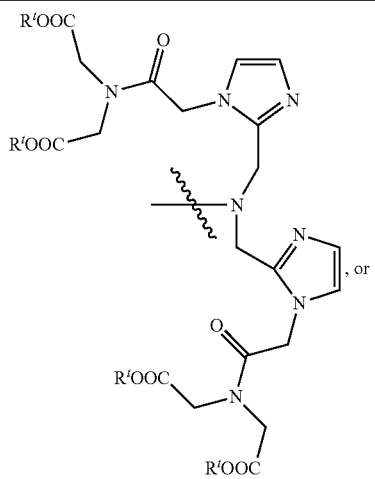

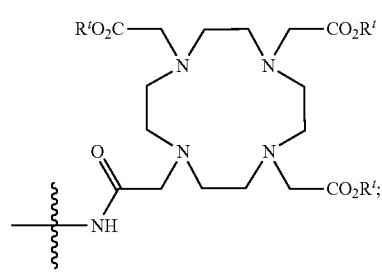

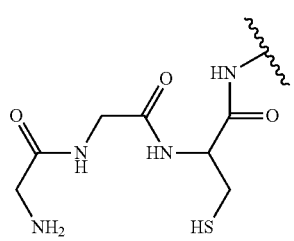

16
-continued

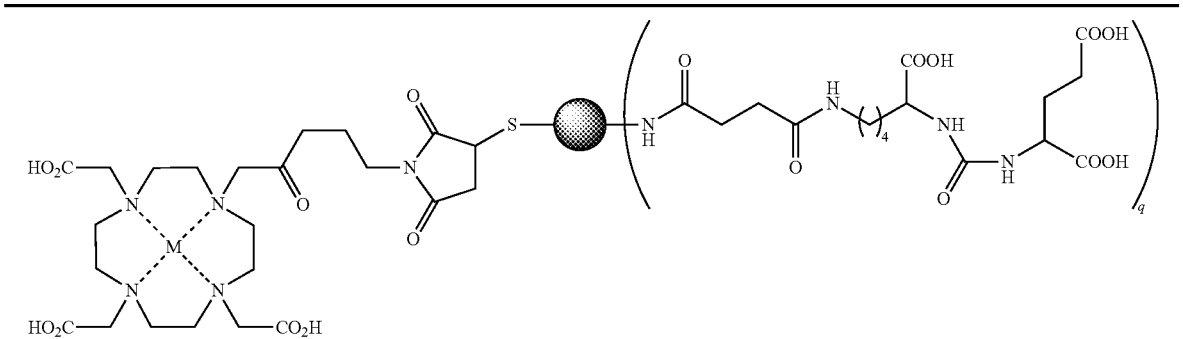

For the structures shown above, $R^t$ is H, a $C_1$-$C_8$ alkyl group, an ammonium ion, an alkylammonium ion, or an alkali or alkaline earth metal ion and $R^v$ is a $C_1$-$C_8$ alkyl.

The inventive dendrimer conjugates should improve the tissue distribution, binding affinity, improve toxicological profile and pharmacokinetics of a Formula I dendrimer conjugate complexed to a radionuclide.

In another embodiment of the present invention, there is provided a complex comprising a metal ion selected from the group consisting of $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{111}$In and $^{188}$Re, and a dendrimer conjugate according to Formula I. Illustrative of an inventive complex without limitation are those which are structurally depicted below in Table 3.

TABLE 3

TABLE 3-continued
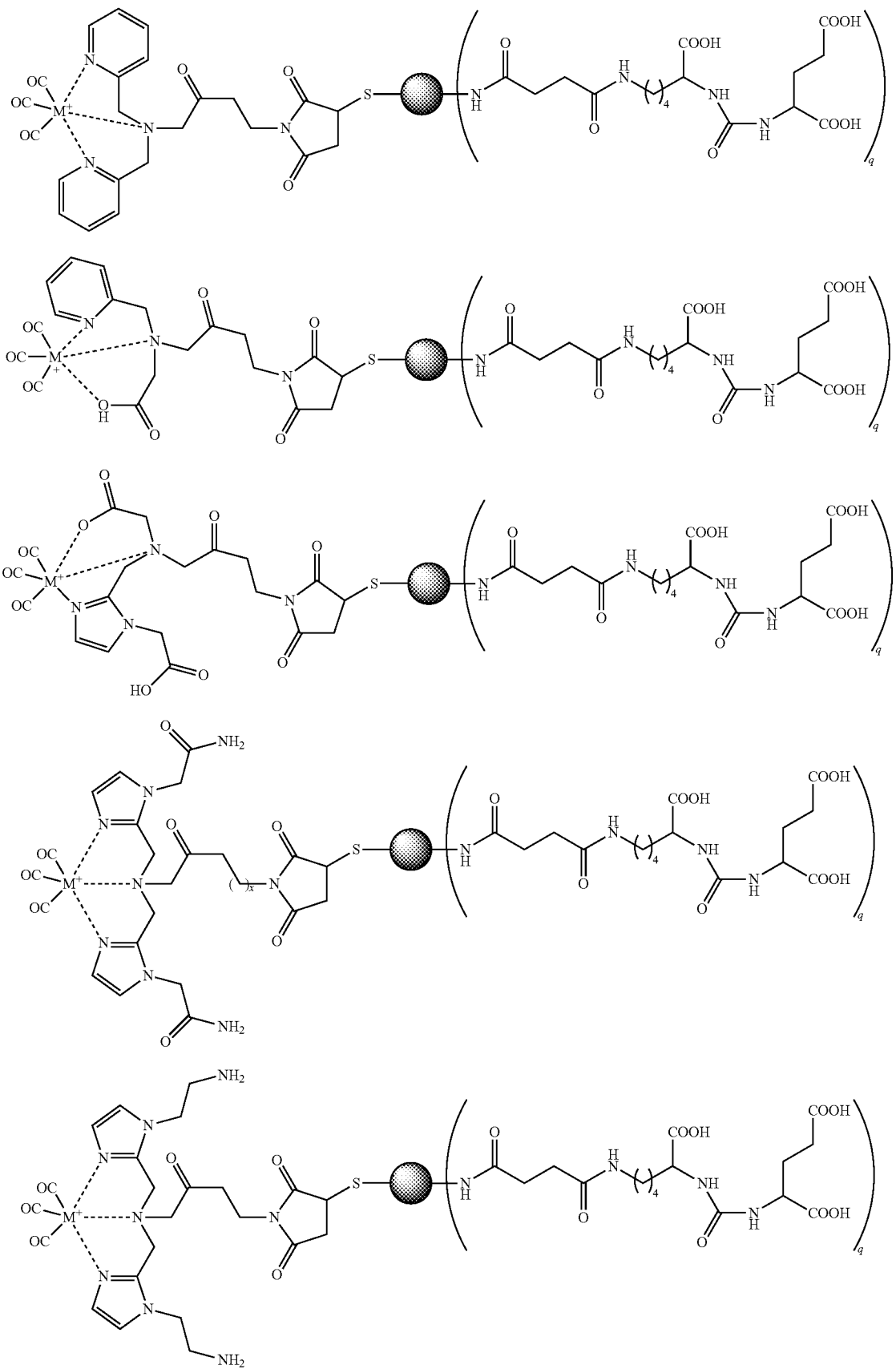

TABLE 3-continued
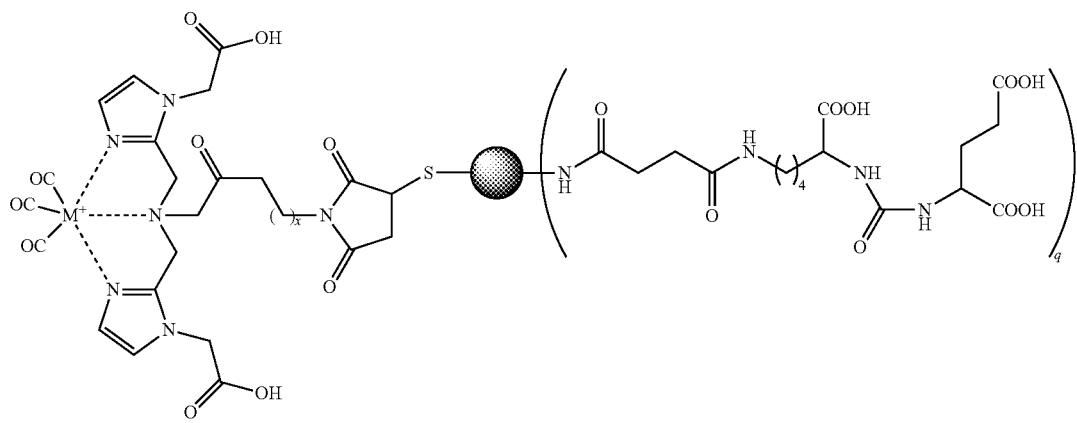
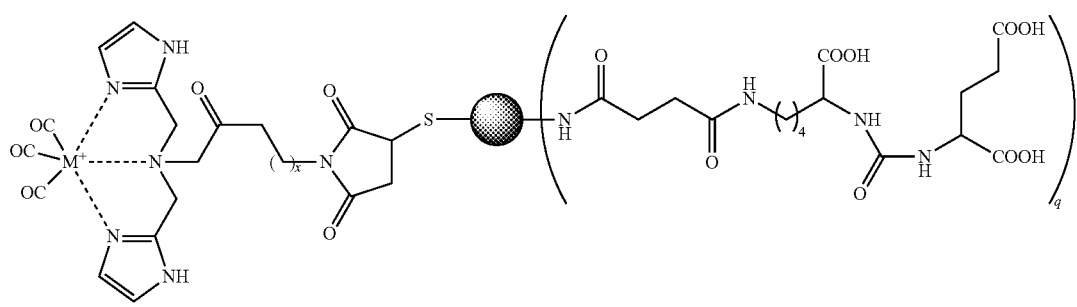
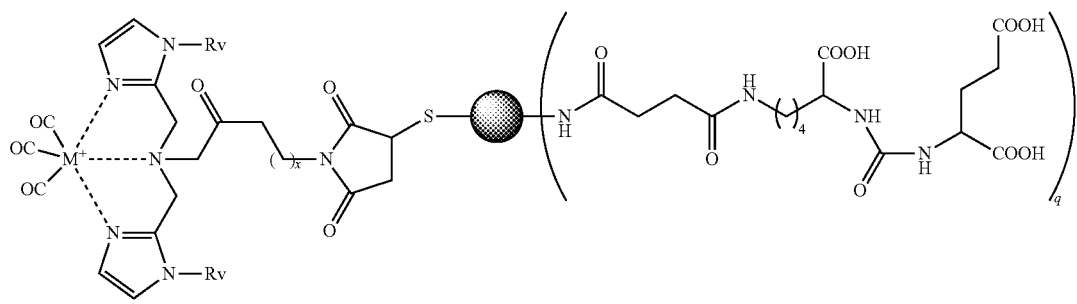
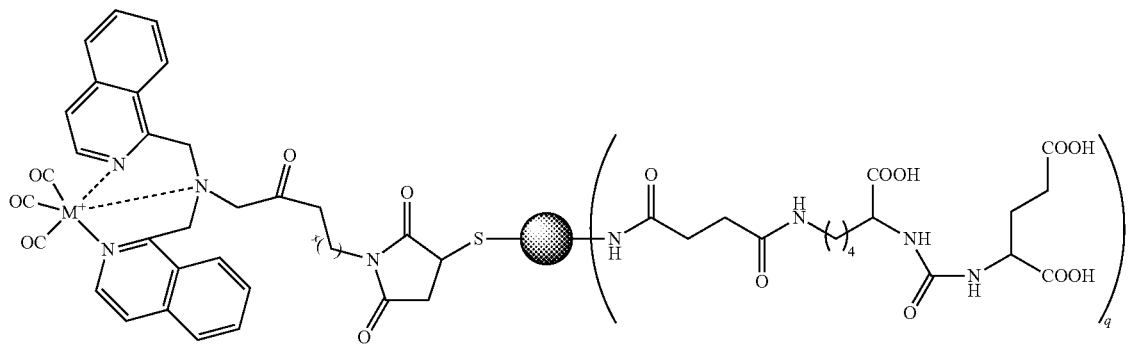
In one embodiment, a complex in accordance with the present invention is a reduced PAMAM dendrimer whose surface succinamic acid residues are conjugated to GUL directly or a GUL-linker analog with a single radioisotope chelating group DOTA attached to the dendrimer through its free sulfhydryl group as shown below.

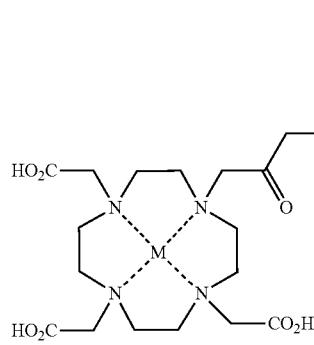
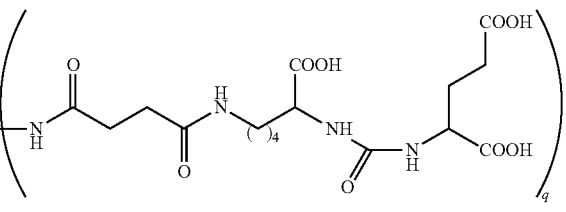

For this complex integer q represents the proportion of surface succinamic acid residues conjugated GUL moieties (Z).

That is, the proportion of available surface groups, X, conjugated to Z; is in the range from about 10% to about 100%, preferably about 10%, 20%, 30%, 40%, 50%, 55%, 60%, 65% 70%, 75%, 80%, 85%, 90%, 92%, 94%, 96%, 98% or 99%. In one embodiment the proportion of available surface groups, X, conjugated to Z is in the range from about 50%, 52%, 54%, 56%, 58%, 60%, 62%, 64%, 66%, 68%, 70%, 72%, 74%, 76%, 78%, 80% 82%, 84%, 86%, or 88%.

Depending on the application for which the inventive complex is to be used, the inventive complex can be chelated to one or more radionuclides suitable for providing radiotherapy or one or more radionuclides suitable for radioimaging and or detection of PSMA expressing tissue. Exemplary radioisotopes without limitation include $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{111}$In and $^{188}$Re.

Accordingly, in one embodiment, a pharmaceutical composition is provided including the inventive complex that includes a metal and the compound of Formula I a salt, solvate, stereoisomer, or tautomer thereof, and a pharmaceutically acceptable carrier.

In general, metal complexes of the compound Formula I or pharmaceutical compositions thereof, may be administered orally, or via a parenteral route, usually by injection. Parenteral routes include, but are not limited to, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. In some embodiments, the compound, or pharmaceutical composition thereof, is administered orally. Such compositions may take the form of tablets, pills, capsules, semisolids, powders, solutions, suspensions, elixirs, aerosols, or any other appropriate compositions.

According to another aspect, a pharmaceutical composition is provided, which is suitable for in vivo imaging. Such suitable imaging pharmaceutical compositions contain an imaging agent that has a radionuclide either as an element, i.e. radioactive iodine, or a radioactive metal chelate complex of the compound of Formula I in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl) aminomethane (and its salts), phosphate, citrate, bicarbonate, etc; sterile water; physiological saline; and balanced ionic solutions containing chloride and or dicarbonate salts or normal blood plasma cations such as calcium, potassium, sodium, and magnesium.

The concentration of the imaging agent in the radiological vehicle should be sufficient to provide satisfactory imaging. For example, when using an aqueous solution, the dosage is about 1.0 to 50 millicuries. The imaging agent should be administered so as to remain in the patient for about 1 to 24 hours, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera. In certain embodiments, a method of imaging a region in a patient includes the steps of: administering to a patient a diagnostically effective amount of a compound complexed with a radionuclide; exposing a region of the patient to radiation; and obtaining an image of the region of the patient. In certain embodiments of the region imaged is the head or thorax. In other embodiments, the compounds and complexes of Formula I target the PSMA protein.

Thus, in some embodiments, a method of imaging tissue such as spleen tissue, kidney tissue, or PSMA-expressing tumor tissue is provided including contacting the tissue with a complex including a radioactive metal and a compound including a group of formula:

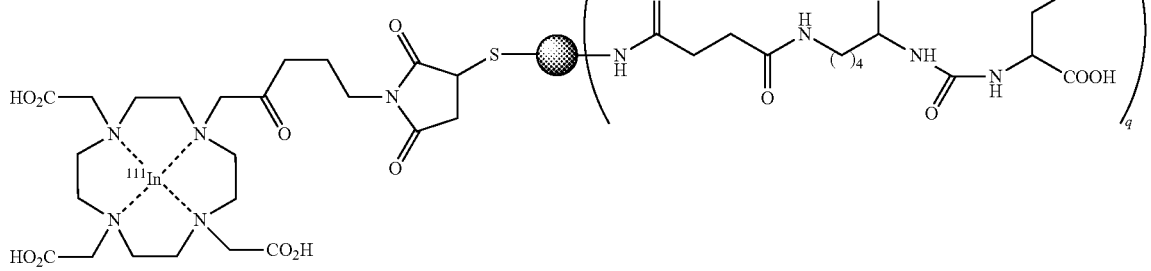

a pharmaceutically acceptable salt or solvate thereof. For a generation 6 dendrimer having 256 surface groups, of which at least 50% are reacted with the PSMA targeting moiety GUL or GUG, q which represents the proportion of available surface groups, X, conjugated to Z (GUL groups), equals 128 unreacted and 128 surface conjugated groups. In other embodiments, the proportion of available surface groups, X, conjugated to Z; can be at 60%, 65% 70%, 75%, 80%, 85%, 90%, 92%, 94%, 96%, 98%, 99% or 100%. For example, the proportion of available surface groups, X, conjugated to Z is at least 50%, 52%, 54%, 56%, 58%, 60%, 62%, 64%, 66%, 68%, 70%, 72%, 74%, 76%, 78%, 80% 82%, 84%, 86%, or 88%. In some embodiments, the tissue targeted by the inventive complex is PSMA-expressing tumor tissue.

In a similar manner, the inventive dendrimer conjugates and complexes can be obtained using generation 1, 2, 3, 4, 5, 6, 7, 8, 9, or 10 dendrimers that have 4, 8, 16, 32, 64, 128, 256, 512, 1024, 2048 and 4096 surface groups respectively. The efficiency of conjugating the PSMA targeting groups (Z) to the surface groups (X) of a dendrimer determines the proportion of surface groups that remain unreacted. Preferably, for any generation od dendrimer that is used to synthesize the inventive conjugates, the proportion of available surface groups, X, conjugated to Z is at least 50%, 52%, 54%, 56%, 58%, 60%, 62%, 64%, 66%, 68%, 70%, 72%, 74%, 76%, 78%, 80% 82%, 84%, 86%, 88%, 90%, 92%, 94%, 96%, 97%, 98% 99% or 100%.

Thus, for the inventive dendrimer conjugates and complexes of these conjugates with radionuclide, the number of dendrimer surface groups between any two consecutive generations n and n+1 can be expressed by the relationship 2m, where m is the number of surface groups for generation n. Thus, for a dendrimer of generation 3 there are 16 surface groups. For the n+1 generation, that is generation 4, the number of surface groups is 2(16) or 32 surface groups.

The present invention, thus generally described, will be understood more readily by reference to the following examples, which are provided by way of illustration and are not intended to be limiting of the present invention.

EXAMPLES

I Synthesis

A. Synthesis of PSMA-Targeting Moiety-EDTA Tetramers

Scheme 1 illustrates the general synthetic route for multimerization of the Glu-urea-lysine based compounds (GUL) using EDTA. The first step, involves the base catalyzed reaction of t-butyl protected GUL with 4,4'-(ethane-1,2-diyl) dimorpholino-2,6-dione to give the t-butyl protected GUL-EDTA dimer. Activation of the remaining two carboxyl groups of the GUL-EDTA dimer using an excess of any of the commercially available peptide coupling reagents, such as without limitation, DCC, HOBt/HBTU, or EDCI and reacting the activated dimer with a slight excess of t-butyl protected GUL gave the desired GUL-EDTA tetramer which was deprotected under mild acidic conditions and subjected to purification. Suitable analytical techniques for purification of the tetramer include, high performance liquid chromatography, preparative thin layer chromatography (TLC), ion exchange chromatography and size exclusion chromatography. Characterization of the purified product can be achieved using $^1$H-NMR spectroscopy, and mass spectrometry.

Scheme 1

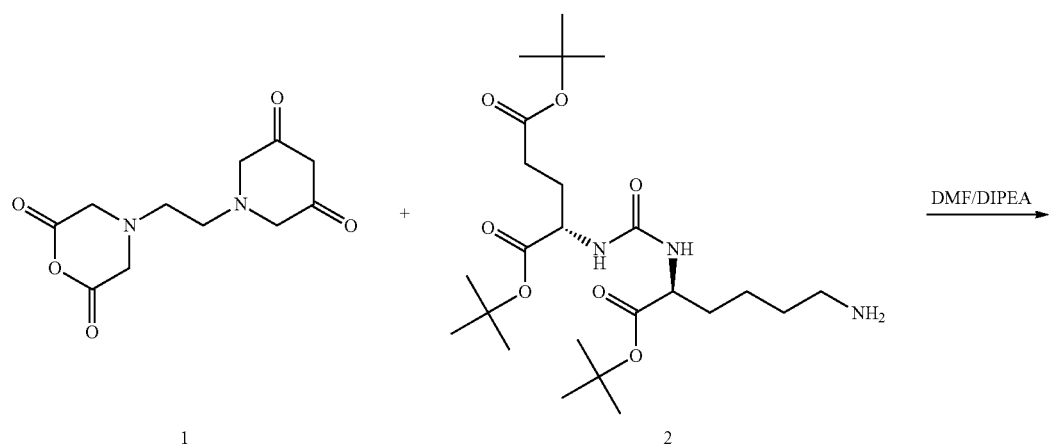

-continued
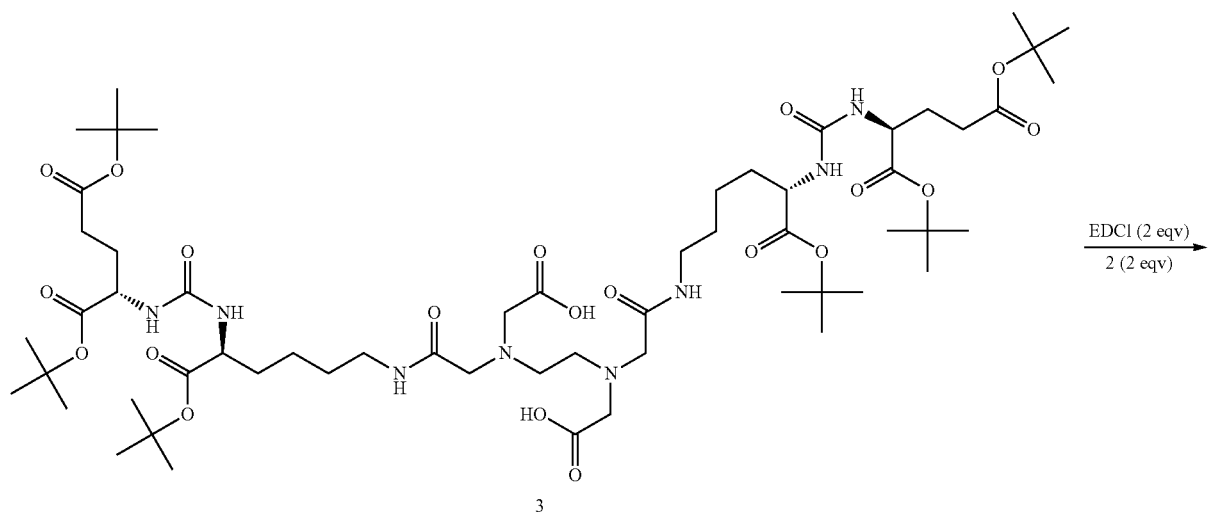
3
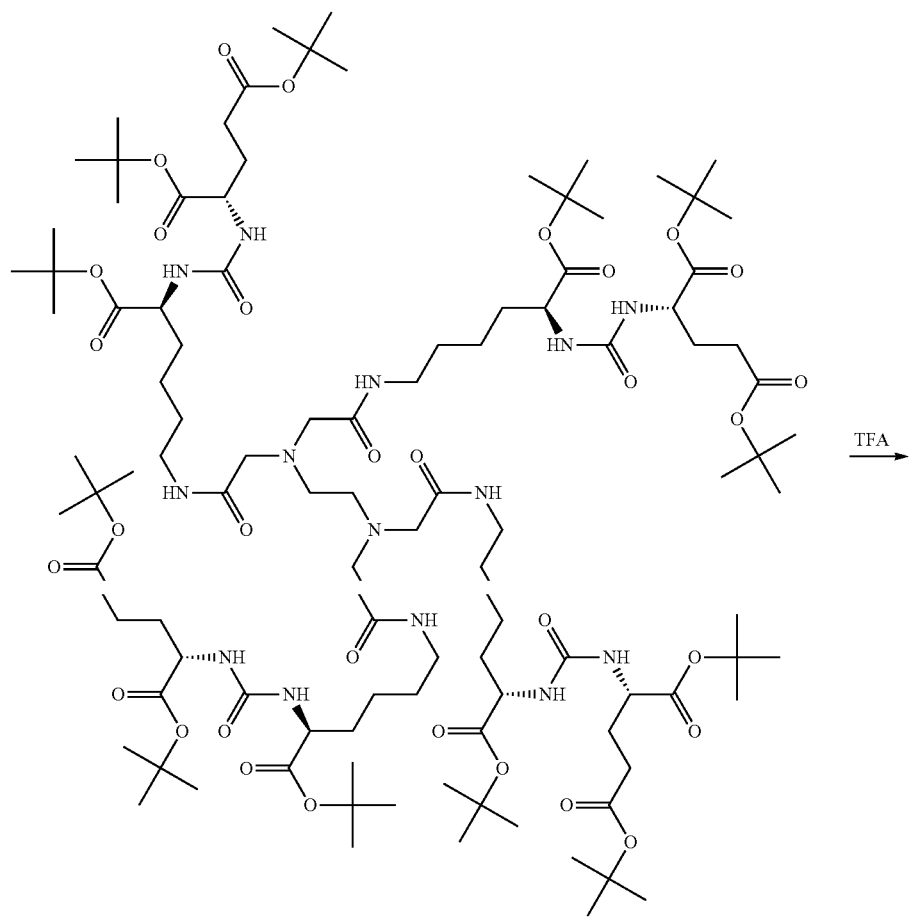
4

-continued
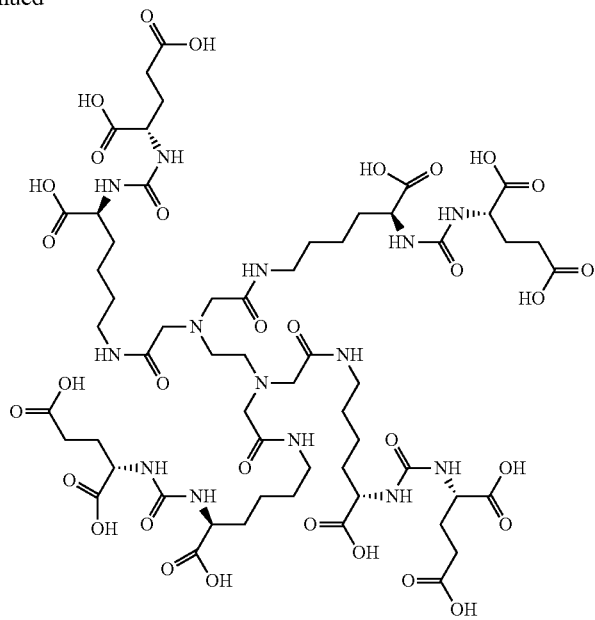
(5)
A similar synthetic strategy is used to tetramerize the GUG-linker-EDTA analog, whose structure is shown below:
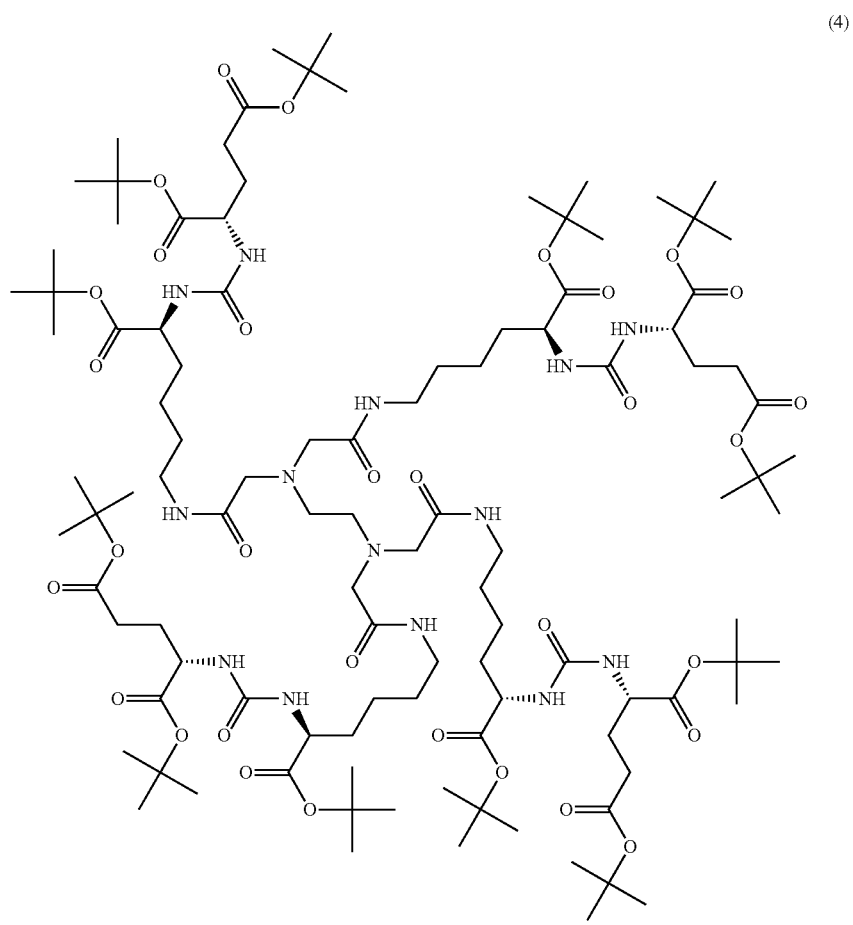 [SMILES: CC(C)(C)OC(=O)CC[C@H](NC(=O)N[C@@H](CCCCNC(=O)CN(CCN(CC(=O)NCCCC[C@H](NC(=O)N[C@@H](CCC(=O)OC(C)(C)C)C(=O)OC(C)(C)C)C(=O)OC(C)(C)C)CC(=O)NCCCC[C@H](NC(=O)N[C@@H](CCC(=O)OC(C)(C)C)C(=O)OC(C)(C)C)C(=O)OC(C)(C)C)CC(=O)NCCCC[C@H](NC(=O)N[C@@H](CCC(=O)OC(C)(C)C)C(=O)OC(C)(C)C)C(=O)OC(C)(C)C)C(=O)OC(C)(C)C)C(=O)OC(C)(C)C]
(4)

(3S,7S,26S,30S)-hexa-tert-butyl 15,18-bis((7S,11S)-7,11-bis(tert-butoxycarbonyl)-2,2-dimethyl-4,9,17-trioxo-3-oxa-8,10,16-triazaoctadecan-18-yl)-5,13,20,28-tetraoxo-4,6,12,15,18,21,27,29-octaazadotriacontane-1,3,7,26,30,32-hexacarboxylate Thus, synthesis of the above GUG-EDTA tetramer was achieved by stirring a solution of (14S,18S)-3-((7S,11S)-7,11-bis(tert-butoxycarbonyl)-2,2-dimethyl-4,9,17-trioxo-3-oxa-8,10,16-triazaoctadecan-18-yl)-14,18-bis(tert-butoxycarbonyl)-6-(carboxymethyl)-23,23-dimethyl-8,16,21-trioxo-22-oxa-3,6,9,15,17-pentaazatetracosan-1-oic acid ((3), 200.0 mg, 0.16 mmol), (S)-di-tert-butyl 2-(3-((S)-6-amino-1-tert-butoxy-1-oxohexan-2-yl)ureido)pentanedioate ((2), 158.0 mg, 0.32 mmol), EDCI (66.0 mg, 0.34 mmol), HOBt (44.0 mg, 0.32 mmol) and DIPEA (0.09 mL) in DCM (5.0 mL,) at room temperature overnight (Scheme 2). The next day, the reaction mixture was concentrated and purified using a Biotage SP4 chromatography system utilizing 0% to 10% methanol in DCM to afford title compound (4) as a white solid. $(M+H/2)^+=1086$.

Scheme 2

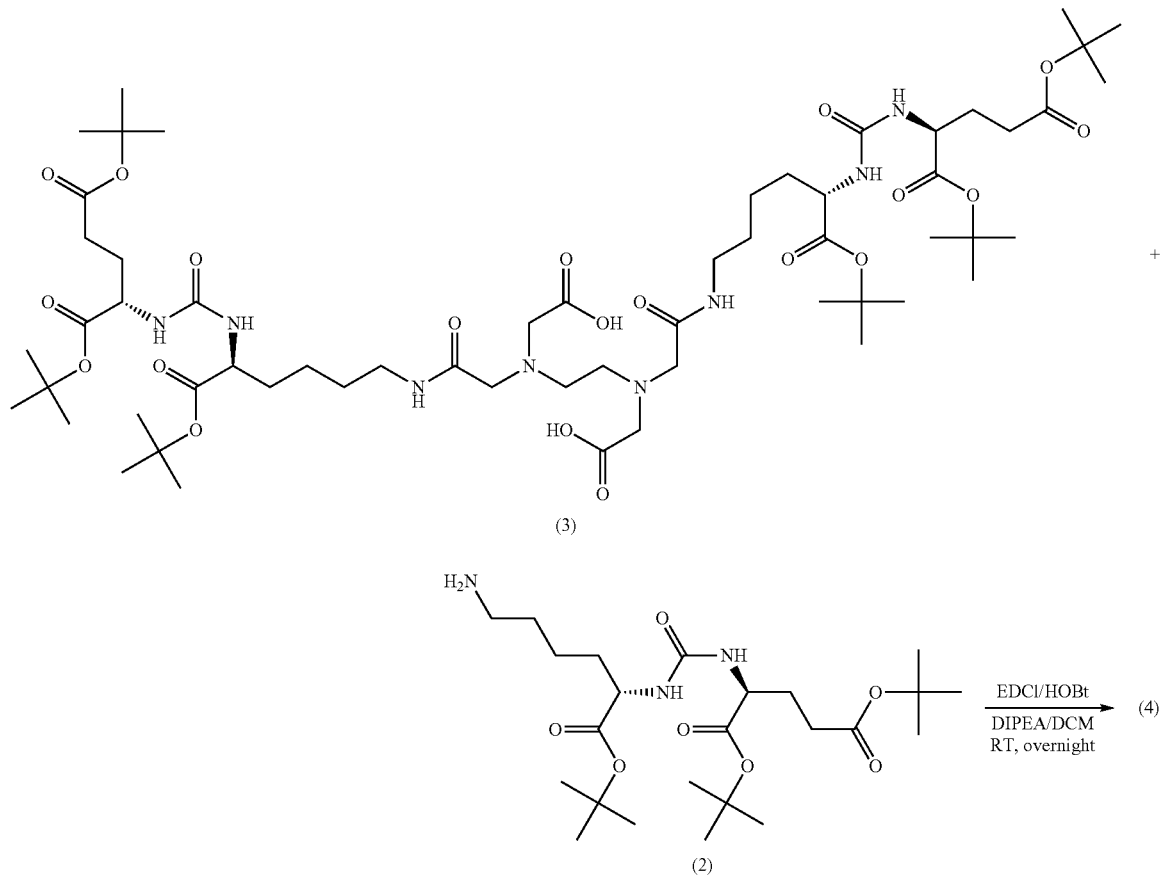

Deprotection of the GUG-EDTA tetramer was achieved by stirring a DCM solution (1.0 ml), of (3S,7S,26S,30S)-hexa-tert-butyl 15,18-bis((7S,11S)-7,11-bis(tert-butoxycarbonyl)-2,2-dimethyl-4,9,17-trioxo-3-oxa-8,10,16-triazaoctadecan-18-yl)-5,13,20,28-tetraoxo-4,6,12,15,18,21,27,29-octaazadotriacontane-1,3,7,26,30,32-hexacarboxylate (4) in TFA (2.0 mL), for 12 hours at room temperature. Evaporation of the solvent afforded the desired crude product (3S,7S,26S,30S)-15,18-bis(2-((S)-5-carboxy-5-(3-((S)-1,3-dicarboxypropyl)ureido)pentylamino)-2-oxoethyl)-5,13,20,28-tetraoxo-4,6,12,15,18,21,27,29-octaazadotriacontane-1,3,7,26,30,32-hexacarboxylic acid (5), which was purified by HPLC. $(M+H)^+=1497$.

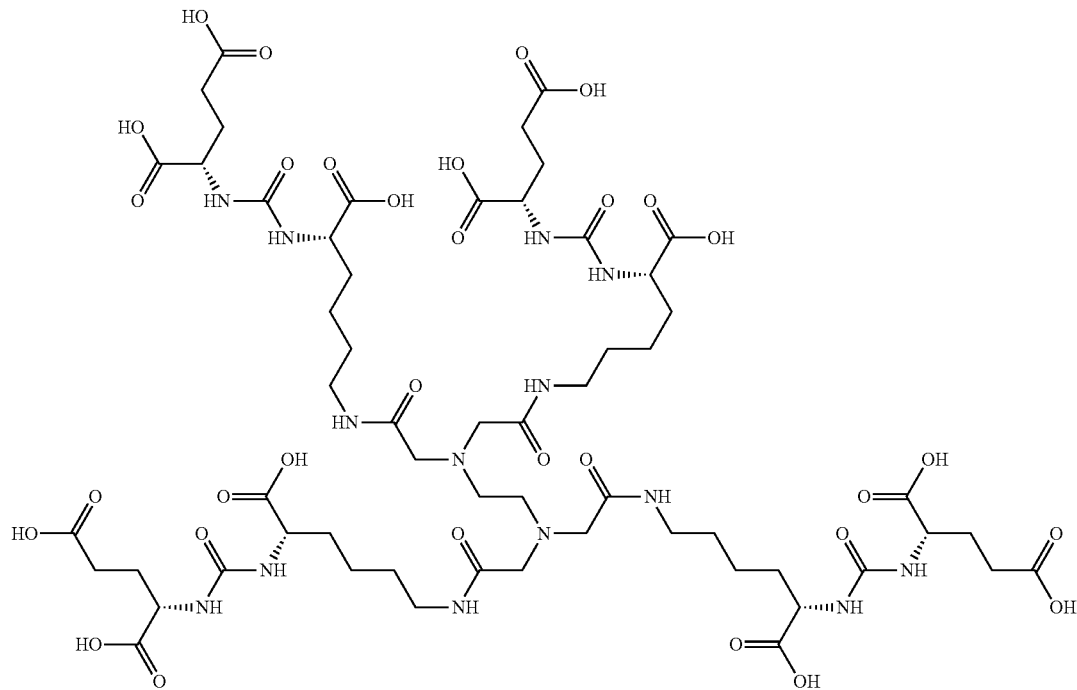

(5)

30

B. Synthesis of PSMA-Targeting Moiety-Dendrimer-Metal Chelator Conjugates

A series of inventive dendrimer conjugates will be synthesized using GUI, GUG or the appropriate GUL-linker or GUG-linker compounds that showed increased binding affinity for PSMA based on binding studies using the EDTA tetramer analogs of these compounds. Conjugation of these high affinity pharmacophore-linker compounds to the surface acid groups of a cystamine core PAMAM dendrimers containing 16-128 surface groups is carried out using the synthetic protocol illustrated below in Scheme 3.

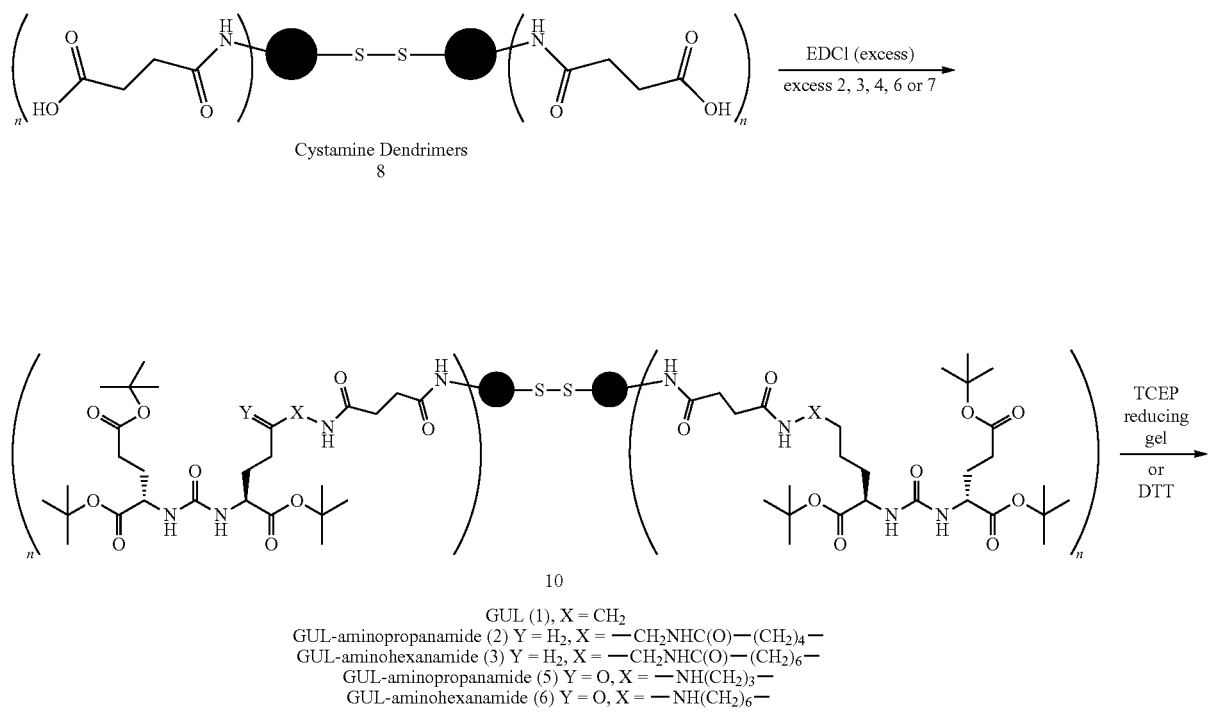

GUL (1), X = CH$_2$
GUL-aminopropanamide (2) Y = H$_2$, X = —CH$_2$NHC(O)—(CH$_2$)$_4$—
GUL-aminohexanamide (3) Y = H$_2$, X = —CH$_2$NHC(O)—(CH$_2$)$_6$—
GUL-aminopropanamide (5) Y = O, X = —NH(CH$_2$)$_3$—
GUL-aminohexanamide (6) Y = O, X = —NH(CH$_2$)$_6$—

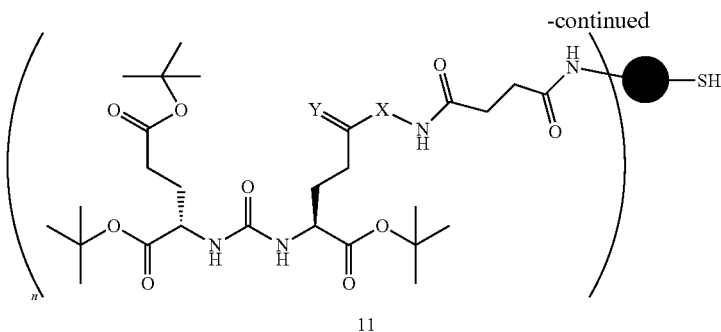

11

-continued

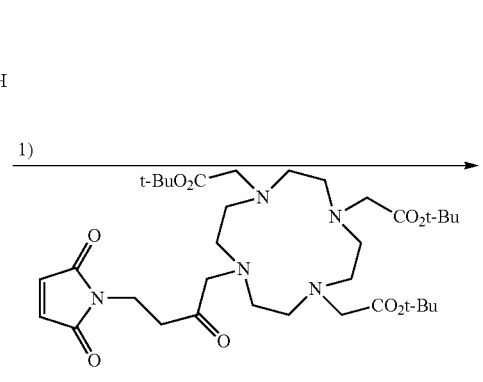

2) TFA

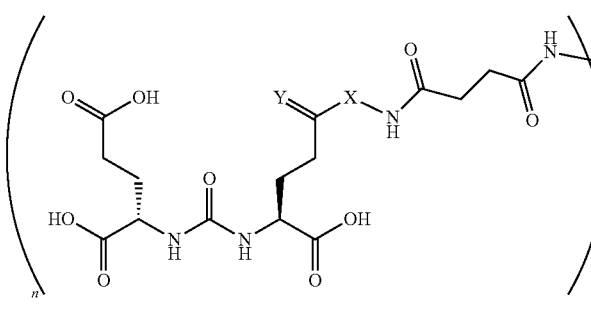

9

| Dendrimer Generation | Surface Group (n) |
|---|---|
| 2 | 8 |
| 3 | 16 |
| 4 | 32 |
| 5 | 64 |
| 6 | 128 |

In general, commercial disulfide cystamine core dendrimers, available with succinamic acid surface groups in generations two through six (8) will be reacted with an excess of an appropriate PSMA-targeting compound, for example, compounds 1, 2, 3, 5 or 6 to afford the protected PSMA dendrimer conjugates (10) which contain the desired PSMA-targeting/recognition units. Conjugation of the PSMA-targeting groups to the dendrimer surface is achieved using an excess of a coupling agent, such as EDCI along with a slight excess of the appropriate PSMA-targeting compound.

The disulfide cystamine core of the dendrimer conjugate will then be chemically reduced to allow conjugation of a single DOTA (metal chelator) moiety to the free sulfhydryl group. Conjugation of DOTA to the free sulfhydryl group will be achieved by using the DOTA-maleimide compound (12). Deprotection of the t-butyl ester groups with TFA will afford the desired Formula I dendrimer conjugates.

In one embodiment, a generation 2, 3, 4, 5, or 6 PAMAM-succinamic acid dendrimers will be used, having 16, 32, 64, 128, or 256 surface groups for conjugation to the PSMA targeting moiety. Using the above described reaction protocol, greater at least 80% of the free surface groups will be conjugated to the PSMA targeting moiety. According to an embodiment of this invention, the conjugation reaction illustrated in Scheme 3 above affords a Formula I dendrimer conjugate in which at least 85%, 90%, 91%, 92%, 93%, 94%, 95%, 96%, 97%, 98%, 99% or 100% of the surface succinamic acid groups are covalently bonded to the PSMA targeting moiety. In another embodiment, the percentage of surface succinamic acid groups covalently bonded to the PSMA targeting moiety is at least 50%, 52%, 54%, 56%, 58%, 60%, 62%, 64%, 66%, 68% or 70%.

Initially, the target molecules will be synthesized as non-radioactive indium derivatives for in vitro characterization and biological assessment. Compounds will be analyzed for purity and confirmation of structure using widely accepted standard analytical techniques ($^1$H NMR spectroscopy and mass spectroscopy (MALDI-TOF), and purity will be assessed by size exclusion chromatography), and screened in vitro in a competitive binding assay for inhibition of [$^{123}$I]-MIP-1072 binding to LNCaP human prostate cancer cells.

The DOTA-dendrimer-PSMA targeting moiety conjugates that exhibit the highest affinity for PSMA will then be complexed to a suitable radionuclide for radio-imaging or radio-therapeutic applications. Thus, radiolabeling of Formula I conjugates to form complexes was accomplished using either the free α-amino acids or as the appropriately N-protected amino acid derivative utilizing the following methodology. The $^{111}$In radiolabeling will be accomplished as follows: To a 10 mL vial containing 10 mCi of indium-111 chloride in a volume of 0.5 mL (0.05 N HCl) is added TraceSelect® Ultra water to obtain a final reaction volume of 1.0 mL. The solution of the radionuclide will be transferred to a vial containing 10 nmoles of a Formula I dedrimer-conjugate. The reaction mixture will be heated at 100° C. for 30 minutes, then cooled to room temperature for a minimum of 5 minutes. The reaction will be diluted to the desired volume by adding sterile saline so as to prepare a sample of the inventive complex that is suitable for injection (0.9% NaCl).

II. Pharmaceutical Formulations

The inventive PSMA-targeting compounds, their conjugates to dendrimers and radionuclide-dendrimer complexes will be useful for inhibiting the expression and/or activity of PSMA as well as the metastasis of prostate cancer. Formula I conjugates and their radionuclide conjugates will also find use in radio-imaging applications used to detect cancer tissue that expresses PSMA.

In one embodiment, the invention will provide a pharmaceutical composition comprising one or more Formula I conjugates or a pharmaceutically acceptable salt, solvate, stereoisomer, tautomer, or prodrug, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In another embodiment, the pharmaceutical formulation will comprise the complex of the inventive dendrimer conjugate and a radionuclide metal along with a pharmaceutically acceptable salt, solvate, stereoisomer, tautomer, or prodrug, in admixture with a pharmaceutically acceptable carrier.

The inventive compositions can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions in accordance with the invention include without limitation tablets, troches, lozenges, aqueous or oily suspensions, dispersible powders or granules, emulsion, hard or soft capsules, syrups or elixirs.

Encompassed within the scope of the invention are pharmaceutical compositions suitable for single unit dosages that comprise a complex of the invention its pharmaceutically acceptable stereoisomer, prodrug, salt, solvate, hydrate, or tautomer and a pharmaceutically acceptable carrier.

Inventive compositions suitable for oral use may be prepared according to any method known to the art for the manufacture of pharmaceutical compositions. For instance, liquid formulations of the inventive complexes contain one or more agents selected from the group consisting of sweetening agents, flavoring agents, coloring agents and preserving agents in order to provide pharmaceutically elegant and palatable preparations of the inventive complex.

For tablet compositions, the active ingredient in admixture with non-toxic pharmaceutically acceptable excipients is used for the manufacture of tablets. Exemplary of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive complex is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensaturatedion products of an alkylene oxide with fatty acids, for example polyoxyethylene stearate, or condensaturatedion products of ethylene oxide with long chain aliphatic alcohols, for example heptadecaethyleneoxycetanol, or condensaturatedion products of ethylene oxide with partial esters derived from fatty acids and a hexitol such as polyoxyethylene sorbitol monoleate, or condensaturatedion products of ethylene oxide with partial esters derived from fatty acids and hexitol anhydrides, for example polyethylene sorbitan monoleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensaturatedion products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The Formula I-radionuclide complexes may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

III. General Biology

A. Testing of EDTA-PSMA Tetramers

The newly prepared analogs of the general structure 5 were screened in a human prostate cancer cell binding assay at a concentration of 3 nM using PSMA positive (+), LnCap cells. The results of this screening demonstrated to us whether the compounds exhibited specific binding to PSMA (+) cells. Compounds that exhibited specific binding to PSMA (+) cells where further evaluated in a competitive binding assay against the PSMA inhibitor (S)-2-(3-((S)-1-carboxy-5-(4-iodobenzylamino)pentyl)ureido)pentanedioic acid (MIP-1072), and $IC_{50}$ values were calculated.

MIP-1072

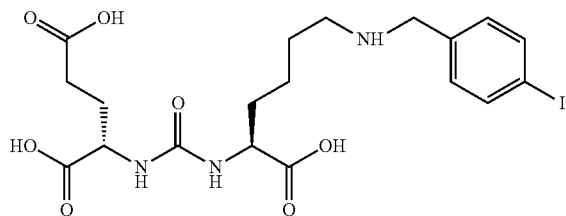

B. In Vitro Preliminary Screening

Human prostate cancer cell line, LNCaP (PSMA positive) were obtained from the American Type Culture Collection (Rockville, Md.). LNCaP cells were maintained in RPMI-1640 medium (Invitrogen, Carlsbad, Calif.) supplemented with 10% fetal bovine serum (Hyclone, Logan, Utah) in a humidified incubator at 37° C./5% $CO_2$. Cells were removed from flasks for passage or for transfer to 12-well assay plates by incubating them with 0.25% trypsin/EDTA (Invitrogen, Carlsbad, Calif.).

In a typical competitive binding assay, LNCaP cells were plated in 12-well plates at approximately $4 \times 10^5$ cells/well and incubated for 48 hours in a humidified incubator at 37° C./5% carbon dioxide prior to addition of PSMA inhibitors. The exemplary EDTA-PSMA tetramer MIP-1444 was diluted in serum-free cell culture medium containing 0.5% bovine serum albumin (BSA). Diluted MIP-1444 was added to the cells in the presence of 3 nM $[^{123}I]$-MIP-1072 for 1 hour at room temperature. Cells were removed from the plates by gently pipetting and transferred to 1.5 mL Eppendorff tubes. Samples were microcentifuged for 30 seconds at 15K×g. The medium was aspirated and the pellet will be washed twice by dispersal in fresh assay medium followed by microcentrifigation. Cell binding of $[^{123}I]$-MIP-1072 was determined by counting the cell pellet in a Wallac 1282 automated gamma counter. Cold MIP-1072 will serve as a positive control in the assay. IC-50 values were generated using GraphPad Prism software.

FIG. 1 illustrate the competitive binding curves for several inventive PSMA targeting moieties as well as conjugates obtained by di- and tetramerization using EDTA. As illustrated in FIG. 1, the PSMA targeting group GUL (MIP-1033), has a low affinity for PSMA, with an $IC_{50}$ value that is 36-fold greater than the $IC_{50}$ for the tetramer MIP-1444. The dimer of GUL (MIP-1046), also exhibits a greater binding affinity for PSMA than MIP1033, with an $IC_{50}$ value ~30-fold lower than the $IC_{50}$ value for MIP-1033. Taken together, these results suggest that multimerization of appropriately spaced GUL or GUG moieties using a dendrimer could provide a suitable strategy for increasing the therapeutic efficacy of radiolabelled GUL and/or GUG-conjugates, by improving tissue distribution, lowering drug uptake by kidneys, and due to the improved pharmacokinetic profile of the inventive dendrimer conjugates.

C. Tissue Distribution

Uptake of $^{111}$In-labeled PSMA-dendrimer complexes in human tumor xenograft models will be performed according to published methods. Briefly, LNCaP cells will be trypsinized, counted, and suspended in a solution containing 50% PBS (with 1 mg/mL D-glucose and 36 μg/mL sodium pyruvate) and 50% Matrigel (BD Biosciences, Franklin Lakes, N.J.). $NCr^{nu/nu}$ mice will be inoculated subcutaneously in the hind flank with $2 \times 10^6$ cells in a 0.25 mL suspension volume. Studies of tumor uptake will be conducted when the tumors reach a size of 100-200 $mm^3$. Tissue uptake will be analyzed by administering, via the tail vein, a bolus injection of approximately 2 μCi/mouse in a constant volume of 0.05 mL. Groups of 5 animals will be euthanized by asphyxiation with carbon dioxide at 1, 4 and 24 hours post injection. Tissues (tumor, blood, heart, liver, lungs, spleen, large and small intestine, stomach, kidneys, skeletal muscle, bone, adipose, testes and brain) will be dissected, excised, weighed wet, transferred to plastic tubes and counted in an automated γ-counter (LKB Model 1282, Wallac Oy, Finland). Tissue time-radioactivity levels will be expressed as % injected dose per gram tissue (% ID/g) and % injected dose per organ (% DPO). Co-injection of 50 mg/kg PMPA will be used to demonstrate specific binding to the target.

D. Therapeutic Treatments

The inventive PSMA-targeting compounds, their conjugates to dendrimers and the inventive radionuclide-dendrimer complexes will be useful for inhibiting the expression and/or activity of PSMA as well as for inhibiting the metastasis of prostate cancer. Formula I conjugates and their radionuclide conjugates also find use in radio-imaging applications used to detect cancer tissue that expresses PSMA.

Compounds, dendrimer conjugates and their complexes to radionuclides in accordance with the present inhibit NAALADase (PSMA), and are thus suitable candidate therapeutics for treatment of diseases that could be receptive to NAALADase inhibition. Exemplary of such diseases include without limitation painful and sensory diabetic neuropathy, neuronal damage and prostate cancer, schizophrenia, colorectal cancer, inflammation, amyotrophic lateral sclerosis, or diabetic neuropathy. Guidance for the modeling of such therapeutic treatments can be found in Goodman & Gilman's The Pharmacological Basis of Therapeutics, McGraw Hill, 10 edition, 2001, Pharmaceutical Preformulation and Formulation: A Practical Guide from Candidate Drug Selection to Commercial Dosage Form, CRC, 2001 and Handbook of Pharmaceutical Excipients, AphA Publications, 5 edition, 2005.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, including the first and last number listed for the range.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:
1. A dendrimer conjugate according to Formula I:

$$\left( R_1 - S - \bigodot - X_p \right) Z_q \qquad I$$

wherein
● represents a dendrimer core of a generation, n, selected from the group consisting of 1, 2, 3, 4, 5, 6, 7, 8; 9 and 10, each generation associated with a predetermined number of surface groups, p;
X is a surface group selected from the group consisting of —COOR' and —NR'R" in its "free" or unconjugated form, and —NHC(O)—$(CH_2)_a$—C(O)—, —NHC(O)—$(C_2-C_6)$alkenyl-C(O), —NHC(O)—$CH_2$—O—$NH_2$, —NHC(O)—$(CH_2)_a$-maleimide, and —NR'—$(CH_2)_a$—NR" in its conjugated form;
S is sulfur;
$R_1$ is a metal chelator;
p is an integer selected from 4, 8, 16, 32, 64, 128, 256, 512, 1024, 2048 and 4096;
Z is a prostate specific membrane antigen targeting moiety according to Formula A:

$$\text{A}$$

wherein
—C=J is —$CH_2$ group or —C=O;
L is selected from the group consisting of —COOR''', —$(CH_2)$—NH—C(O)—CH(O)—, —$(CH_2)$—NH—C(O)—$(CH_2$—$CH_2$—O$)_y$—NR'—, —$(CH_2)$—NH—C(O)—$(CH_2)_z$—NR'—; and —$(CH_2)$—NH—C(O)—$(CH_2)_z$—SH—;
R', R", R''', $R_2$, $R_3$, and $R_4$ are each independently selected from the group consisting of H, and straight or branched $C_1$-$C_6$ alkyl;
q represents the proportion of available surface groups, X, conjugated to Z, and q is from 10% to 100%;
subscripts a, y and z are each independently integers between 0 and 8 inclusive.

2. The dendrimer conjugate according to claim 1, wherein X is —NHC(O)—$(CH_2)_a$C(O)— and Z is a Formula A compound, wherein —C=J is —$CH_2$ and L-$(CH_2)$—NH—C(O)—$(CH_2)_z$—NR'—.

3. The dendrimer conjugate according to claim 2, wherein a is 2 and z is 3.

4. The dendrimer conjugate according to claim 1, wherein a is 2 and z is 6.

5. The dendrimer conjugate according to claim 1, wherein X is —NR'—(CH$_2$)$_a$—NR"— and Z is a Formula A compound, wherein —C=J is —C=O and L is —COOR'".

6. The dendrimer conjugate according to claim 5, wherein a is an integer between 1 and 3 inclusive.

7. The dendrimer conjugate according to claim 6, wherein a is 2.

8. The dendrimer conjugate according to claim 5, wherein X is —NH—(CH$_2$)$_2$—NH— and L is a —COO—(C$_1$-C$_6$) alkyl.

9. The dendrimer conjugate according to claim 1, wherein the proportion of available surface groups, X, conjugated to Z is in the range from about 50% to about 100%.

10. The dendrimer conjugate according to claim 9, wherein the proportion of available surface groups, X, conjugated to Z is in the range from about 50% to about 75%.

11. The dendrimer conjugate according to claim 1, wherein R$_1$ is

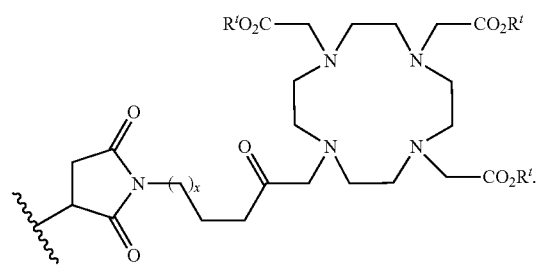

12. The dendrimer conjugate according to claim 9, wherein R$_1$ is

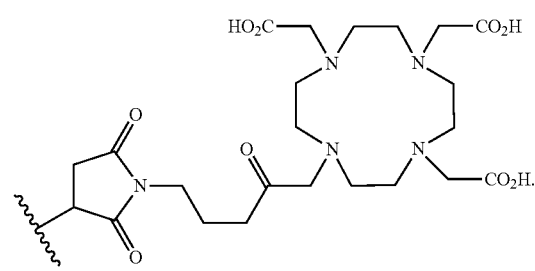 [SMILES: *C1CC(=O)N(CCCC(=O)CN2CCN(CC(=O)O)CCN(CC(=O)O)CCN(CC(=O)O)CC2)C1=O]

13. A complex comprising:
(i) a metal ion; and
(ii) a dendrimer conjugate according to according to Formula I:

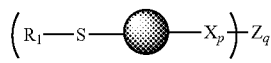
I wherein
● represents a dendrimer core of a generation, n, selected from the group consisting of 1, 2, 3, 4, 5, 6, 7, 8; 9 and 10, each generation associated with a predetermined number of surface groups, p;

X is a surface group selected from the group consisting of —COOR' and —NR'R" in its "free" or unconjugated form, and —NHC(O)—(CH$_2$)$_a$—C(O)—, —NHC(O)—(C$_2$-C$_6$)alkenyl-C(O), —NHC(O)—CH$_2$—O—NH$_2$, —NHC(O)—(CH$_2$)$_a$-maleimide, and —NR'—(CH$_2$)$_a$—NR" in its conjugated form;

S is sulfur;

R$_1$ is a metal chelator;

p is an integer selected from 4, 8, 16, 32, 64, 128, 256, 512, 1024, 2048 and 4096;

Z is a prostate specific membrane antigen targeting moiety according to Formula A:

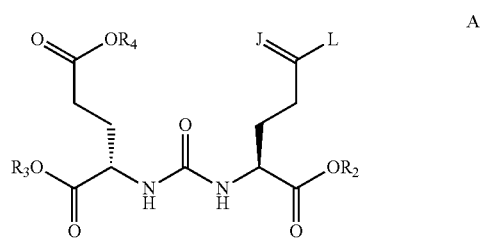
A wherein
—C=J is —CH$_2$ group or —C=O;
L is selected from the group consisting of —COOR"', —(CH$_2$)—NH—C(O)—CH(O)—, —(CH$_2$)—NH—C(O)—(CH$_2$—CH$_2$—O)$_y$—NR'—, —(CH$_2$)—NH—C(O)—(CH$_2$), —NR'—; and —(CH$_2$)—NH—C(O)—(CH$_2$)$_z$—SH—;
R', R", R'", R$_2$, R$_3$, and R$_4$ are each independently selected from the group consisting of H, and straight or branched C$_1$-C$_6$ alkyl;
q represents the proportion of available surface groups, X, conjugated to Z, and q is from 10% to 100%;
subscripts a, y and z are each independently integers between 0 and 8 inclusive.

14. The complex according to claim 13, wherein the metal is selected from the group consisting of $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{111}$In and $^{188}$Re.

15. The complex according to claim 13, wherein R$_1$ is

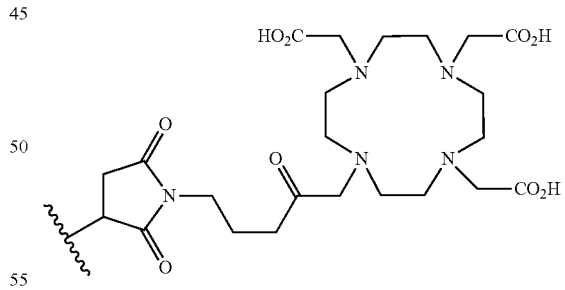

and the metal ion is selected from the group consisting of $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{111}$In and $^{188}$Re.

16. The complex according to claim 15, wherein the metal ion is $^{111}$In.

17. The complex according to claim 13, wherein the proportion of available surface groups, X, conjugated to Z is in the range from about 50% to about 100%.

18. The complex according to claim 17, wherein the proportion of available surface groups, X, conjugated to Z is in the range from about 50% to about 75%.

19. The complex according to claim 13, that is selected from the following table:
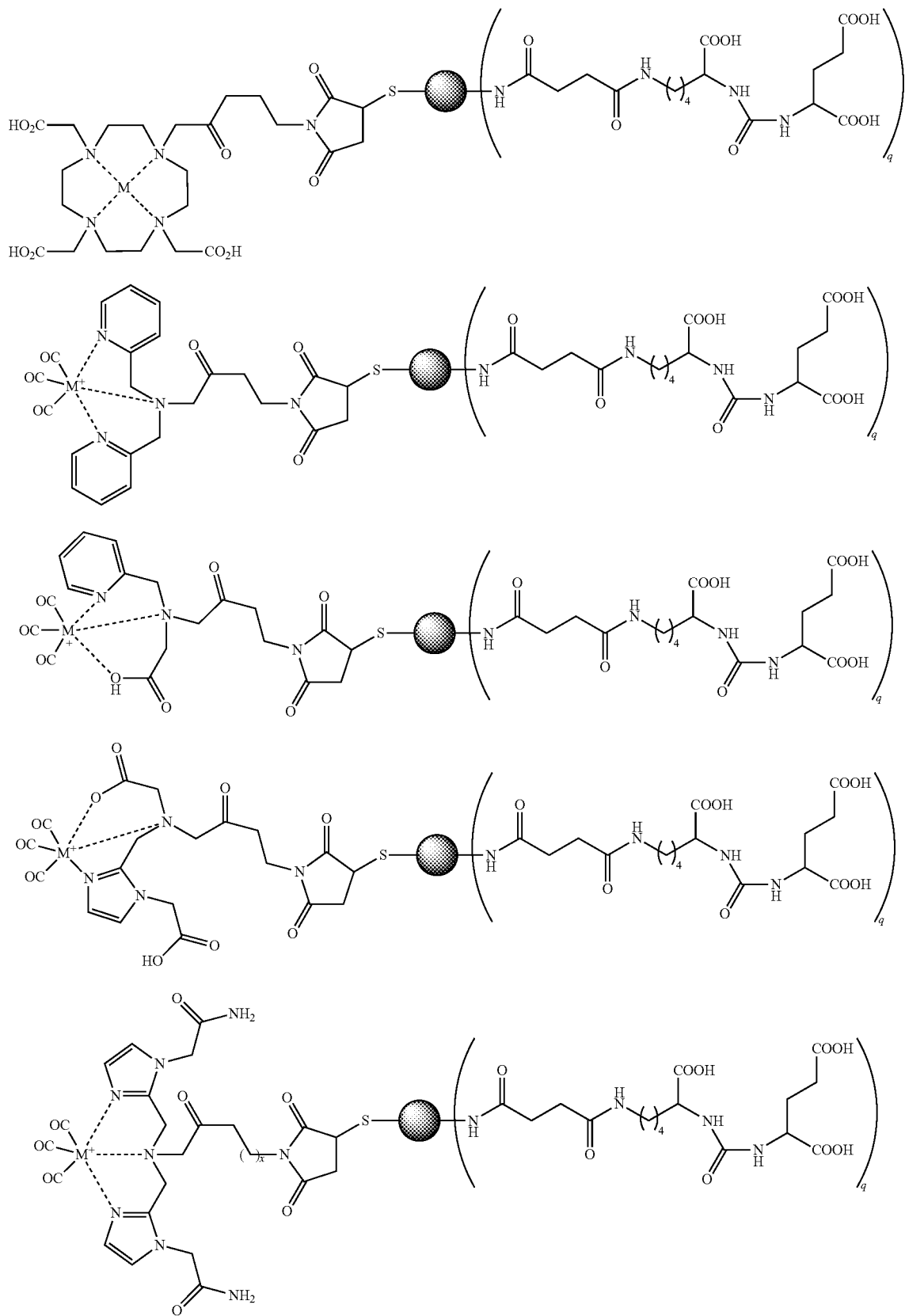

-continued
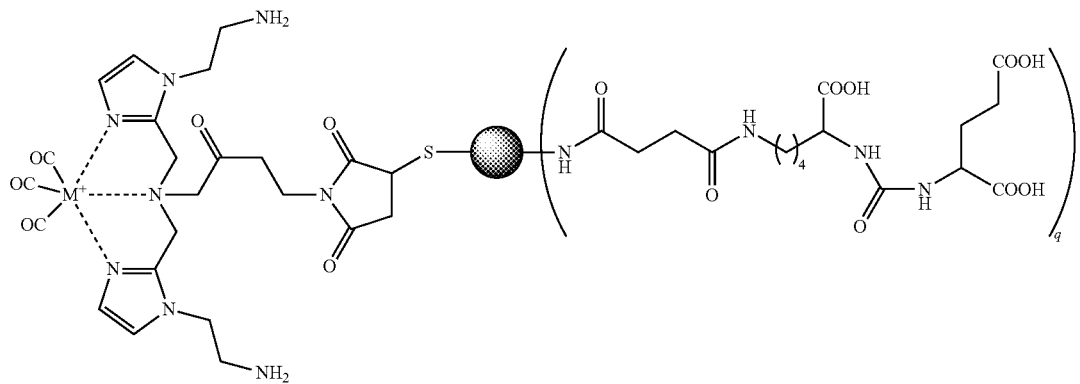
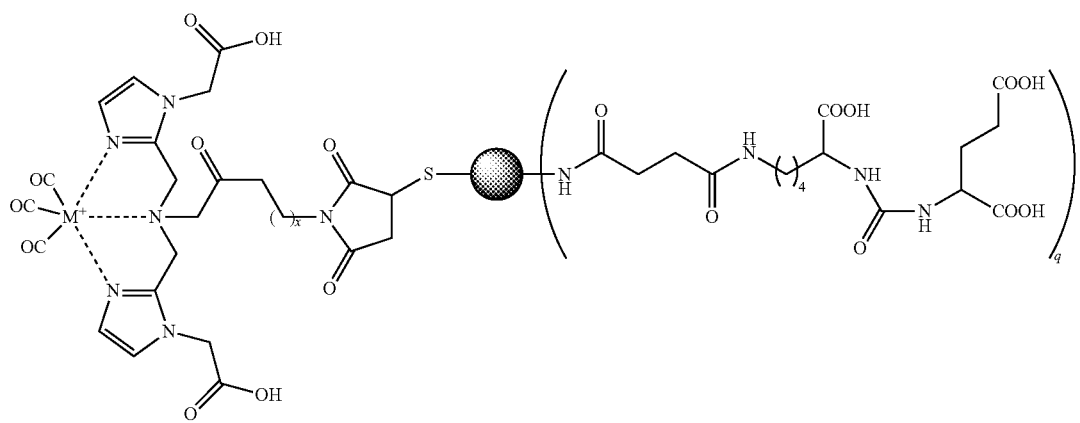
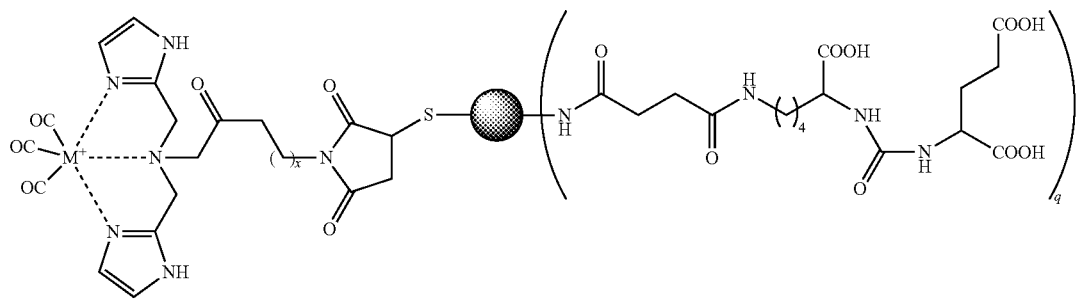
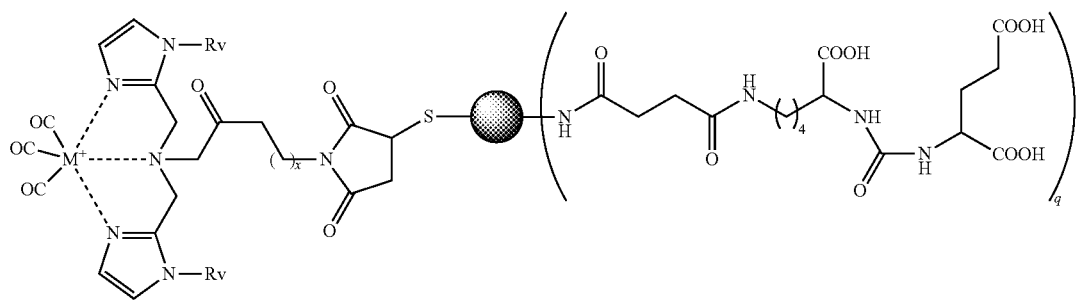

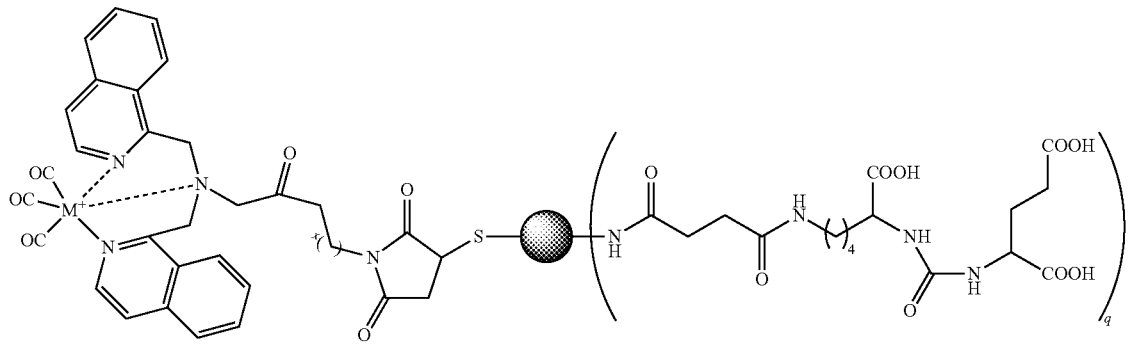

wherein
M is selected from the group consisting of $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{111}$In and $^{188}$Re;
x is an integer between 0 and 6 inclusive; and
a pharmaceutically acceptable salt or solvate thereof.

20. The pharmaceutical formulation, comprising the complex according to claim 13, a pharmaceutically acceptable salt or solvate thereof, and a pharmaceutically acceptable excipient.

21. The pharmaceutical formulation according to claim 20, wherein the complex is

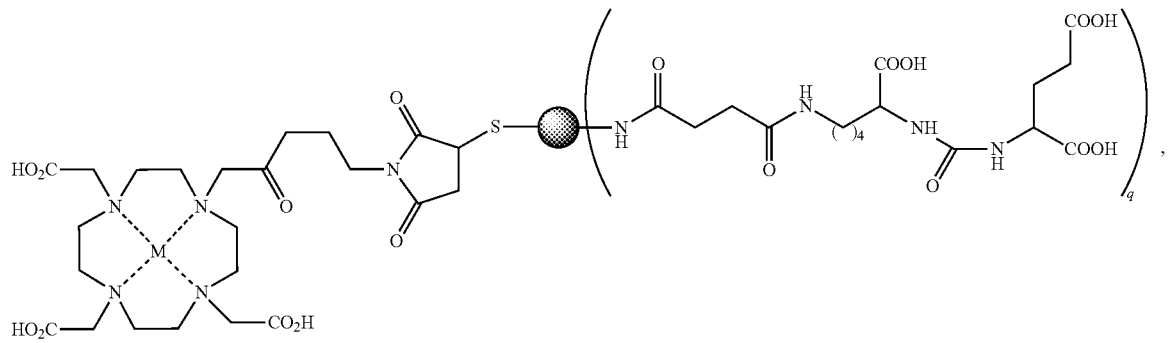

M is selected from the group consisting of $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{111}$In and $^{188}$Re;
a pharmaceutically acceptable salt or solvate thereof, and a pharmaceutically acceptable excipient.

22. The method of treating prostate cancer in a patient, comprising administering to a patient a therapeutically effective amount of a pharmaceutical composition of the complex according to claim 13, or a pharmaceutically acceptable salt or solvate thereof in which M is selected from the group consisting of $^{68}$Ga, $^{64}$Cu, $^{67}$Cu, $^{212}$Pb, $^{203}$Pb, $^{212}$Bi, $^{213}$Bi, $^{89}$Zr, $^{186}$Re, $^{99m}$Tc, $^{90}$Y, $^{86}$Y, $^{177}$Lu, $^{111}$In and $^{188}$Re.

23. The method of imaging prostate cancer tissue in a patient, comprising administering to a patient a diagnostically effective amount of a pharmaceutical composition of the complex according to claim 13, or a pharmaceutically acceptable salt or solvate thereof in which M is selected from the group consisting of $^{68}$Ga, $^{111}$In, $^{99m}$Tc and $^{186}$Re, and obtaining an image of said prostate tissue.

24. The method of claim 22, wherein the tissue is PSMA-expressing prostate cancer tissue.

25. The method of claim 23, wherein the tissue is PSMA-expressing prostate cancer tissue.

* * * * *